US012740581B2

(12) United States Patent
Fotsing et al.

(10) Patent No.: US 12,740,581 B2
(45) Date of Patent: Sep. 22, 2026

(54) AMIDE COMPOUNDS AND THEIR USE AS FLAVOR MODIFIERS

(71) Applicant: Firmenich Incorporated, Plainsboro, NJ (US)

(72) Inventors: Joseph R. Fotsing, San Diego, CA (US); Melissa Sue Wong, San Diego, CA (US)

(73) Assignee: Firmenich Incorporated, Plainsboro, NJ (US)

( * ) Notice: Subject to any disclaimer, the term of this patent is extended or adjusted under 35 U.S.C. 154(b) by 362 days.

(21) Appl. No.: 18/547,112

(22) PCT Filed: Apr. 20, 2022

(86) PCT No.: PCT/US2022/025569
§ 371 (c)(1),
(2) Date: Aug. 18, 2023

(87) PCT Pub. No.: WO2022/231908
PCT Pub. Date: Nov. 3, 2022

(65) Prior Publication Data

US 2024/0156140 A1 May 16, 2024

Related U.S. Application Data

(60) Provisional application No. 63/179,751, filed on Apr. 26, 2021.

(51) Int. Cl.
*A23L 27/00* (2016.01)
*A23L 27/20* (2016.01)
*C07C 233/83* (2006.01)

(52) U.S. Cl.
CPC ............ *A23L 27/88* (2016.08); *A23L 27/204* (2016.08); *C07C 233/83* (2013.01)

(58) Field of Classification Search
CPC ...... A23L 27/32; A23L 27/204; C07C 233/83
See application file for complete search history.

(56) References Cited

U.S. PATENT DOCUMENTS 2,809,895 A 10/1957 Swisher
3,041,180 A 6/1962 Swisher
(Continued)

FOREIGN PATENT DOCUMENTS

CN 103619191 3/2014
CN 103648303 3/2014
(Continued)

OTHER PUBLICATIONS

James R. Piper, Lucy M. Rose, Thomas P. Johnston, and Marie M. Grenan, J. of Med. Chem 1979 22 (6), 631-639 (Year: 1979).*
(Continued)

*Primary Examiner* — Michele L Jacobson
(74) *Attorney, Agent, or Firm* — Knobbe, Martens, Olson & Bear, LLP

(57) ABSTRACT

The present disclosure generally provides amide compounds, including cinnamic acid amides, and the use of such compounds and related compounds as flavor modifiers. In some aspects, the disclosure provides compositions that include such amide compounds, such as compositions that include such amide compounds and one or more additional compounds, such as a sweetener, a salt, a glutamate, an arginate, a purinic ribonucleotide, and the like. In some other aspects, the disclosure provides methods of reducing or eliminating the amount of sweetener, salt, glutamate, or arginate in a food or beverage product.

13 Claims, 1 Drawing Sheet

(56) References Cited

U.S. PATENT DOCUMENTS

| | | | |
|---|---|---|---|
| 3,704,137 | A | 11/1972 | Beck |
| 4,610,890 | A | 9/1986 | Miller et al. |
| 4,689,235 | A | 8/1987 | Barnes et al. |
| 5,603,971 | A | 2/1997 | Porzio et al. |
| 5,786,017 | A | 7/1998 | Blake et al. |
| 5,897,897 | A | 4/1999 | Porzio et al. |
| 6,416,799 | B1 | 7/2002 | Porzio et al. |
| 6,468,576 | B1 | 10/2002 | Sher et al. |
| 6,607,771 | B2 | 8/2003 | Benczedi et al. |
| 6,932,982 | B2 | 8/2005 | McIver et al. |
| 7,488,503 | B1 | 2/2009 | Porzio et al. |
| 8,076,491 | B2 | 12/2011 | Karanewsky et al. |
| 8,124,121 | B2 | 2/2012 | Tachdjian et al. |
| 8,445,692 | B2 | 5/2013 | Karanewsky et al. |
| 8,541,421 | B2 | 9/2013 | Tachdjian et al. |
| 8,592,592 | B2 | 11/2013 | Tachdjian et al. |
| 8,735,081 | B2 | 5/2014 | Li et al. |
| 8,815,956 | B2 | 8/2014 | Tachdjian et al. |
| 8,877,922 | B2 | 11/2014 | Tachdjian et al. |
| 8,968,708 | B2 | 3/2015 | Tachdjian et al. |
| 8,993,027 | B2 | 3/2015 | Prakash et al. |
| 9,000,051 | B2 | 4/2015 | Feltin et al. |
| 9,000,054 | B2 | 4/2015 | Tachdjian et al. |
| 9,247,759 | B2 | 2/2016 | Karanewsky et al. |
| 9,394,287 | B2 | 7/2016 | Priest et al. |
| 9,834,544 | B2 | 12/2017 | Tachdjian et al. |
| 10,421,727 | B2 | 9/2019 | Chumakova et al. |
| 2007/0128234 | A1 | 6/2007 | Subramaniam et al. |
| 2010/0172945 | A1 | 7/2010 | Gregson et al. |
| 2012/0027866 | A1 | 2/2012 | Gregson et al. |
| 2014/0056836 | A1 | 2/2014 | Subramaniam et al. |
| 2015/0164117 | A1 | 6/2015 | Kaplan et al. |
| 2016/0235102 | A1 | 8/2016 | Oglesby |
| 2016/0346752 | A1 | 12/2016 | Struillou et al. |
| 2017/0119032 | A1 | 5/2017 | Patron et al. |
| 2018/0103667 | A1 | 4/2018 | Womack et al. |
| 2018/0369777 | A1 | 12/2018 | Shi et al. |
| 2019/0082727 | A1 | 3/2019 | Van Sleeuwen et al. |

FOREIGN PATENT DOCUMENTS

| | | |
|---|---|---|
| WO | WO 2012/146584 | 11/2012 |
| WO | 2021/063942 | 4/2021 |

OTHER PUBLICATIONS

National Academy of Sciences, 1965, Chemicals Used in Food Processing, publication 1274, pp. 63-258.

Boonen et al., J. Ethnopharmacol., vol. 142, pp. 563-590 (2012).

Ariyoshi et al., bull. Chem. Soc. Japan, vol. 47, pp. 326-330 (1974).

Int'l Search Report & Written Opinion of Int'l Searching Authority, PCT App. No. PCT/US2022/025569, dated Oct. 10, 2022.

* cited by examiner

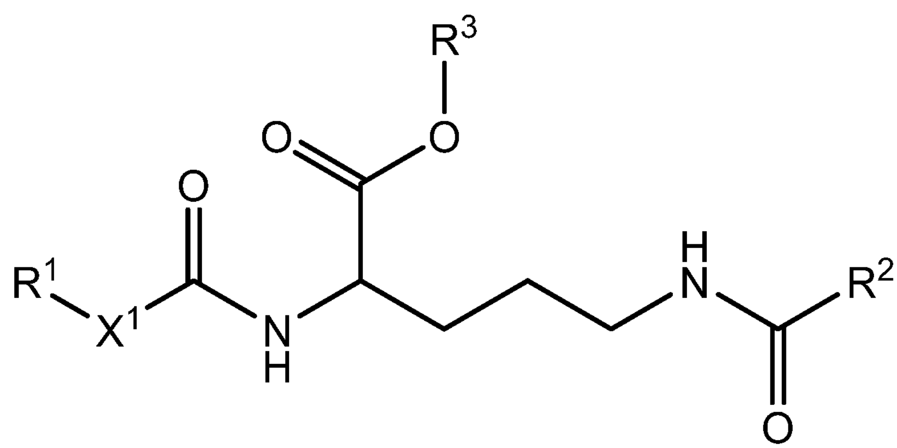

AMIDE COMPOUNDS AND THEIR USE AS FLAVOR MODIFIERS

TECHNICAL FIELD

The present disclosure generally provides amide compounds, including cinnamic acid amides, and the use of such compounds and related compounds as flavor modifiers. In some aspects, the disclosure provides compositions that include such amide compounds, such as compositions that include such amide compounds and one or more additional compounds, such as a sweetener, a salt, a glutamate, an arginate, a purinic ribonucleotide, and the like. In some other aspects, the disclosure provides methods of reducing or eliminating the amount of sweetener, salt, glutamate, or arginate in a food or beverage product.

DESCRIPTION OF RELATED ART

The taste system provides sensory information about the chemical composition of the external world. Taste transduction is one of the more sophisticated forms of chemically triggered sensation in animals. Signaling of taste is found throughout the animal kingdom, from simple metazoans to the most complex of vertebrates. Mammals are believed to have five basic taste modalities: sweet, bitter, sour, salty, and umami/kokumi.

Umami is the taste most commonly associated with the savory taste of monosodium glutamate (MSG), meat products, cheeses, tomatoes, mushrooms, soy sauce, fish sauce, miso, and the like. Mammals generally perceive umami to be a pleasurable sensation. Kokumi is a related taste commonly associated with the taste of fermented products, soy sauce, fish sauce, and shrimp paste. Many of these typical sources of umami and kokumi taste are high in glutamic acid and salt, or rely on animal products.

Excessive sodium intake can cause a number of health-related problems. One such problem is hypertension. Hypertension is a condition in which the pressure of the blood against artery walls is high enough that it may eventually cause heart disease and other health problems. Excessive sodium intake also adversely affect the balance of water and minerals in the body. For example, excessive sodium intake can cause calcium loss, which can lead to osteoporosis and other problems. Excessive consumption of food products containing glutamic acid can also have certain adverse health effects, as glutamic acid interferes with the functioning of neurotransmitters. Thus, it is generally desirable to reduce the consumption of sodium and glutamic acid. Further, there is increased consumer demand for food and beverage products that do not contain animal-derived ingredients, such as animal-derived fats, meat products, or dairy products.

Enhancement of salt, umami, or kokumi flavors provides an alternative approach to partially or completely replacing ingredients that are traditionally used to impart salt, umami, and/or kokumi taste. Even so, there is a limited number of compounds, especially naturally derived compounds, that can accomplish this effectively. Thus, there is a continuing need to discover new compounds having utility as flavor modifiers, especially compounds that enhance, among other flavors, the taste of salt, umami, kokumi, or any combination thereof.

SUMMARY

The present disclosure relates to the discovery that certain compounds exhibit a desirable and surprising effect of enhancing umami and/or salty flavor when used in a food or beverage product.

In a first aspect, the disclosure provides flavor-modifying compounds, where the taste-modifying compounds are compounds of formula (I):

(I)

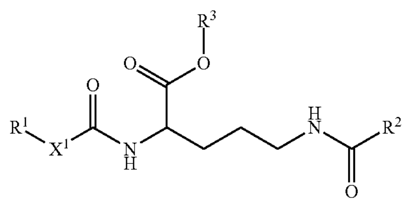

or a comestibly acceptable salt thereof;

wherein:

$R^1$ is $C_{6-14}$ aryl or $C_{4-12}$ heteroaryl, each of which is optionally substituted one or more times by substituents selected independently from the group consisting of $R^Y$;

$R^2$ is a $C_{1-10}$ alkyl, $C_{2-20}$ alkenyl, $C_{6-14}$ aryl, or $C_{1-12}$ heteroaryl, wherein the alkyl and alkenyl groups are each optionally substituted one or more times by substituents selected independently from the group consisting of $R^X$, and wherein the aryl and heteroaryl groups are each optionally substituted one or more times by substituents selected independently from the group consisting of $R^Y$;

$R^3$ is a hydrogen atom or is $C_{1-6}$ alkyl, which is optionally substituted one or more times by —OH, —O—($C_{1-6}$ alkyl), or any combination thereof;

$X^1$ is a direct bond, $C_{1-6}$ alkylene, or $C_{2-6}$ alkenylene, wherein the alkylene and alkenylene groups are each optionally substituted one or more times by substituents selected independently from the group consisting of $R^X$;

$R^X$ is a halogen atom, oxo, —CN, nitro, —OH, —$NH_2$, —C(O)H, —O—C(O)H, —C(O)—OH, —NH—C(O)H, —C(O)—$NH_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, and ($C_{1-6}$ alkoxy)-$C_{1-6}$ alkyl; and $R^Y$ is a halogen atom, oxo, —CN, nitro, —OH, —$NH_2$, —C(O)H, —O—C(O)H, —C(O)—OH, —NH—C(O)H, —C(O)—$NH_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl, $C_{1-6}$ alkyl, and $C_{2-6}$ alkenyl, wherein any adjacent substituents on an aryl or heteroaryl ring can optionally combine to form a fused carbocyclic or heterocyclic ring having from 5 to 7 members.

In a second aspect, the disclosure provides uses of any flavor-modifying compounds of the first aspect, and any embodiments thereof. In a related aspect, the disclosure provides corresponding methods of using any flavor-modifying compounds of the first aspect, and any embodiments thereof, comprising introducing the flavor modifying compounds to an ingestible composition. In some embodiments, the ingestible composition is a flavored product such as a flavored food or beverage product.

In a third aspect, the disclosure provides uses of any compounds of the first aspect, and any embodiments thereof, to modify a flavor of an ingestible composition. In a related aspect, the disclosure provides corresponding methods of using any flavor-modifying compounds of the first aspect, and any embodiments thereof, to modify the flavor of an ingestible composition, comprising introducing the flavor modifying compounds to an ingestible composition. In some embodiments, the ingestible composition is a flavored product such as a flavored food or beverage product.

In a fourth aspect, the disclosure provides uses of any compounds of the first aspect, and any embodiments thereof, to enhance a salty taste of an ingestible composition. In related aspects, the disclosure provides uses of any compounds of the first aspect, and any embodiments thereof, to reduce the salt (e.g., sodium chloride) content of an ingestible composition. In a related aspect, the disclosure provides corresponding methods of using any flavor-modifying compounds of the first aspect, and any embodiments thereof, to enhance a salty taste of an ingestible composition, comprising introducing the flavor modifying compounds to an ingestible composition. In some embodiments of these aspects, the ingestible composition comprises sodium chloride, potassium chloride, or any combination thereof. In some embodiments, the ingestible composition is a flavored product such as a flavored food or beverage product.

In a fifth aspect, the disclosure provides uses of any compounds of the first aspect, and any embodiments thereof, to enhance an umami taste of an ingestible composition. In related aspects, the disclosure provides uses of any compounds of the first aspect, and any embodiments thereof, to reduce or eliminate the glutamate or aspartate content of an ingestible composition. In related aspects, the disclosure provides corresponding methods of using any flavor-modifying compounds of the first aspect, and any embodiments thereof, to enhance an umami taste of an ingestible composition, comprising introducing the flavor modifying compounds to an ingestible composition. In some embodiments of these aspects, the ingestible composition is free or substantially free (for example, no more than 1000 ppm) of monosodium glutamate (MSG). In some embodiments, the ingestible composition is a flavored product such as a flavored food or beverage product.

In a sixth aspect, the disclosure provides uses of any compounds of the first aspect, and any embodiments thereof, to enhance a kokumi taste of an ingestible composition. In a related aspect, the disclosure provides uses of any compounds of the first aspect, or any embodiments thereof, to reduce or eliminate glutamyl (e.g., L-glutamyl peptides) content of an ingestible composition. In another related aspect, the disclosure provides uses of any compounds of the first aspect, or any embodiments thereof, to reduce or eliminate animal (e.g., animal broth or meat) content of an ingestible composition. In a related aspect, the disclosure provides corresponding methods of using any flavor-modifying compounds of the first aspect, and any embodiments thereof, to enhance a kokumi taste of an ingestible composition, comprising introducing the flavor modifying compounds to an ingestible composition. In some embodiments, the ingestible composition is a flavored product such as a flavored food or beverage product.

In a seventh aspect, the disclosure provides ingestible compositions comprising any compounds of the first aspect. In some embodiments, the compounds of the first aspect make up at least 0.10% by weight, or at least 0.5% by weight, or at least 1.0% by weight, of the compositions on a dry weight basis (e.g., based on the total weight of the composition excluding the weight of any liquid carrier). In some embodiments, the concentration of the compounds of the first aspect in the ingestible composition range from 0.1 ppm to 1000 ppm, or from 0.5 ppm to 500 ppm. In some embodiments, the ingestible composition comprises a salty tastant, an umami tastant, a kokumi tastant, or any combination thereof.

In an eighth aspect, the disclosure provides solid-state compositions comprising any compounds of the first aspect, wherein the compounds of the first aspect make up at least 0.1% by weight, or at least 0.5% by weight, or at least 1.0% by weight, of the solid-state compositions, based on the total weight of composition.

In a ninth aspect, the disclosure provides ingestible compositions comprising any compounds of the first aspect, wherein the concentration of the compounds of the first aspect in the ingestible compositions ranges from 1 to 1000 ppm. In some embodiments, the ingestible composition is not a naturally occurring composition.

In a tenth aspect, the disclosure provides a concentrated flavoring composition comprising any compounds of the first aspect.

In an eleventh aspect, the disclosure provides flavored products comprising any compositions of the preceding four aspects. In some embodiments, the flavored products are beverage products, such as soda, flavored water, tea, broth, and the like. In some other embodiments, the flavored products are food products, such as yogurt, soup, and the like. In some embodiments, the flavored product is a mat analogue product.

Further aspects, and embodiments thereof, are set forth below in the Detailed Description, the Drawings, the Abstract, and the Claims.

BRIEF DESCRIPTION OF THE DRAWINGS

The following drawings are provided for purposes of illustrating various embodiments of the compositions and methods disclosed herein. The drawings are provided for illustrative purposes only, and are not intended to describe any preferred compositions or preferred methods, or to serve as a source of any limitations on the scope of the claimed inventions.

FIG. 1 shows chemical formulas representing compounds disclosed herein, wherein: $R^1$ is $C_{6-14}$ aryl or $C_{4-12}$ heteroaryl, each of which is optionally substituted; $R^2$ is a $C_{1-10}$ alkyl, $C_{2-20}$ alkenyl, $C_{6-14}$ aryl, or $C_{1-12}$ heteroaryl, each of which is optionally substituted; $R^3$ is a hydrogen atom or an optionally substituted $C_{1-6}$ alkyl group; and $X^1$ is a direct bond, $C_{1-6}$ alkylene, or $C_{2-6}$ alkenylene, wherein the alkylene and alkenylene groups are each optionally substituted.

DETAILED DESCRIPTION

The following Detailed Description sets forth various aspects and embodiments provided herein. The description is to be read from the perspective of the person of ordinary skill in the relevant art. Therefore, information that is well known to such ordinarily skilled artisans is not necessarily included.

Definitions

The following terms and phrases have the meanings indicated below, unless otherwise provided herein. This disclosure may employ other terms and phrases not expressly defined herein. Such other terms and phrases have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary As used herein, "solvate" means a compound formed by the interaction of one or more solvent molecules and one or more compounds described herein. In some embodiments, the solvates are ingestibly acceptable solvates, such as hydrates.

As used herein, "$C_a$ to $C_b$" or "$C_{a-b}$" in which "a" and "b" are integers, refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

As used herein, "halogen" or "halo" means any one of the radio-stable atoms of column 7 of the Periodic Table of the Elements, such as fluorine, chlorine, bromine, or iodine. In some embodiments, "halogen" or "halo" refer to fluorine or chlorine.

As used herein, "alkyl" means a straight or branched hydrocarbon chain that is fully saturated (i.e., contains no double or triple bonds). In some embodiments, an alkyl group has 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like. Unless indicated to the contrary, the term "alkyl" refers to a group that is not further substituted. Note that the terms "butyl," "pentyl," "hexyl," and the like refer to straight-chain moieties (and do not encompass branched-chain moieties), unless otherwise indicated to the contrary.

As used herein, "heteroalkyl" means a straight or branched hydrocarbon chain containing one or more heteroatoms, that is, an element other than carbon, including but not limited to, nitrogen, oxygen, and sulfur, in the chain backbone. In some embodiments, the heteroalkyl group has from 1 to 20 carbon atom, although the present definition also covers the occurrence of the term "heteroalkyl" where no numerical range is designated. The heteroalkyl group may also be a medium size heteroalkyl having 1 to 9 carbon atoms. The heteroalkyl group could also be a lower heteroalkyl having 1 to 4 carbon atoms. The heteroalkyl group may be designated as "$C_{1-4}$ heteroalkyl" or similar designations. The heteroalkyl group may contain one or more heteroatoms. By way of example only, "$C_{1-4}$ heteroalkyl" indicates that there are one to four carbon atoms in the heteroalkyl chain and additionally one or more heteroatoms in the backbone of the chain. Unless indicated to the contrary, the term "heteroalkyl" refers to a group that is not further substituted.

As used herein, "alkenyl" means a straight or branched hydrocarbon chain containing one or more double bonds. In some embodiments, the alkenyl group has from 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4-yl. Typical alkenyl groups include, but are in no way limited to, ethenyl, propenyl, butenyl, pentenyl, and hexenyl, and the like. Unless indicated to the contrary, the term "alkenyl" refers to a group that is not further substituted.

As used herein, "alkylene" means a branched or straight chain fully saturated di-radical chemical group containing only carbon and hydrogen that is attached to the rest of the molecule via two points of attachment (i.e., an alkanediyl). In some embodiments, the alkylene group has from 1 to 20 carbon atoms, although the present definition also covers the occurrence of the term alkylene where no numerical range is designated. The alkylene group may also be a medium size alkylene having 1 to 9 carbon atoms. The alkylene group could also be a lower alkylene having 1 to 4 carbon atoms. The alkylene group may be designated as "$C_{1-4}$ alkylene" or similar designations. By way of example only, "$C_{1-4}$ alkylene" indicates that there are one to four carbon atoms in the alkylene chain, i.e., the alkylene chain is selected from the group consisting of methylene, ethylene, ethan-1,1-diyl, propylene, propan-1,1-diyl, propan-2,2-diyl, 1-methyl-ethylene, butylene, butan-1,1-diyl, butan-2,2-diyl, 2-methyl-propan-1,1-diyl, 1-methyl-propylene, 2-methyl-propylene, 1,1-dimethyl-ethylene, 1,2-dimethyl-ethylene, and 1-ethyl-ethylene. Unless indicated to the contrary, the term "alkylene" refers to a group that is not further substituted.

As used herein, "alkenylene" means a straight or branched chain di-radical chemical group containing only carbon and hydrogen and containing at least one carbon-carbon double bond that is attached to the rest of the molecule via two points of attachment. In some embodiments, the alkenylene group has from 2 to 20 carbon atoms, although the present definition also covers the occurrence of the term alkenylene where no numerical range is designated. The alkenylene group may also be a medium size alkenylene having 2 to 9 carbon atoms. The alkenylene group could also be a lower alkenylene having 2 to 4 carbon atoms. The alkenylene group may be designated as "$C_{2-4}$ alkenylene" or similar designations. By way of example only, "$C_{2-4}$ alkenylene" indicates that there are two to four carbon atoms in the alkenylene chain, i.e., the alkenylene chain is selected from the group consisting of ethenylene, ethen-1,1-diyl, propenylene, propen-1,1-diyl, prop-2-en-1,1-diyl, 1-methyl-ethenylene, but-1-enylene, but-2-enylene, but-1,3-dienylene, buten-1,1-diyl, but-1,3-dien-1,1-diyl, but-2-en-1,1-diyl, but-3-en-1,1-diyl, 1-methyl-prop-2-en-1,1-diyl, 2-methyl-prop-2-en-1,1-diyl, 1-ethyl-ethenylene, 1,2-dimethyl-ethenylene, 1-methyl-propenylene, 2-methyl-propenylene, 3-methyl-propenylene, 2-methyl-propen-1,1-diyl, and 2,2-dimethyl-ethen-1,1-diyl. Unless indicated to the contrary, the term "alkenylene" refers to a group that is not further substituted.

As used herein, "aromatic" means a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" means an aromatic ring or ring system (i.e., two or more fused rings that share two adjacent carbon atoms) containing only carbon in the ring backbone. When the aryl is a ring system, every ring in the system is aromatic. In some embodiments, the aryl group has from 6 to 18 carbon atoms, although the present definition also covers the occurrence of the term "aryl" where no numerical range is designated. In some embodiments, the aryl group has from 6 to 10 carbon atoms. The aryl group may be designated as "$C_{6-10}$ aryl," "$C_6$-$C_{10}$ aryl," or similar designations. Examples of aryl groups include, but are not limited to, phenyl, naphthyl, azulenyl, and anthracenyl. In some embodiments, the term "aryl" refers to phenyl. Unless indicated to the contrary, the term "aryl" refers to a group that is not further substituted As used herein "aralkyl" or "arylalkyl" means an aryl group connected, as a substituent, via an alkylene group, such as "$C_{7-14}$ aralkyl" and the like, including, but not limited to, benzyl, 2-phenylethyl, 3-phenylpropyl, and the like. In some embodiments, the alkylene group is a lower alkylene group (i.e., a $C_{1-4}$ alkylene group).

As used herein, "heteroaryl" means an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. In some embodiments, the heteroaryl group has from 5 to 18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has from 5 to 10 ring members or from 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl. Unless indicated to the contrary, the term "hereoaryl" refers to a group that is not further substituted.

As used herein, "carbocyclyl" or "carbocyclic ring" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. In some embodiments, the carbocyclyl group has from 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_{3-6}$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2]octanyl, adamantyl, and spiro[4.4]nonanyl. Unless indicated to the contrary, the term "carbocyclyl" refers to a group that is not further substituted.

As used herein, "heterocyclyl" or "heterocyclic ring" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. In some embodiments, the heterocyclyl group has from 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as $—CH_2—$, $—CH_2CH_2—$, $—CH_2CH(CH_3)CH_2—$, and the like.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

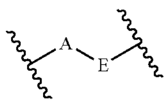

includes the substituent being oriented such that the A is attached at the leftmost attachment point of the molecule as well as the case in which A is attached at the rightmost attachment point of the molecule.

As used herein, a squiggly bond adjacent to a carbon-carbon double bond indicates that the substituents around the carbon-carbon double bond may connect in either an E or Z configuration, or a combination of molecules in either configuration.

As used herein, the singular forms “a,” “an,” and “the” include plural referents unless the context clearly dictates otherwise. For example, reference to “a substituent” encompasses a single substituent as well as two or more substituents, and the like.

As used herein, “for example,” “for instance,” “such as,” or “including” are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, “comprise” or “comprises” or “comprising” or “comprised of” refer to groups that are open, meaning that the group can include additional members in addition to those expressly recited. For example, the phrase, “comprises A” means that A must be present, but that other members can be present too. The terms “include,” “have,” and “composed of” and their grammatical variants have the same meaning. In contrast, “consist of” or “consists of” or “consisting of” refer to groups that are closed. For example, the phrase “consists of A” means that A and only A is present.

As used herein, “optionally” means that the subsequently described event(s) may or may not occur. In some embodiments, the optional event does not occur. In some other embodiments, the optional event does occur one or more times.

As used herein, “or” is to be given its broadest reasonable interpretation, and is not to be limited to an either/or construction. Thus, the phrase “comprising A or B” means that A can be present and not B, or that B is present and not A, or that A and B are both present. Further, if A, for example, defines a class that can have multiple members, e.g., $A_1$ and $A_2$, then one or more members of the class can be present concurrently.

As used herein, certain substituents or linking groups having only a single atom may be referred to by the name of the atom. For example, in some cases, the substituent “—H” may be referred to as “hydrogen” or “a hydrogen atom,” the substituent “—F” may be referred to as “fluorine” or “a fluorine atom,” and the linking group “—O—” may be referred to as “oxygen” or “an oxygen atom.”

Points of attachment for groups are generally indicated by a terminal dash (—) or by an asterisk (*). For example, a group such as *—$CH_2$—$CH_3$ or —$CH_2$—$CH_3$ both represent an ethyl group.

Chemical structures are often shown using the “skeletal” format, such that carbon atoms are not explicitly shown, and hydrogen atoms attached to carbon atoms are omitted entirely. For example, the structure

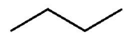

represents butane (i.e., n-butane). Furthermore, aromatic groups, such as benzene, are represented by showing one of the contributing resonance structures. For example, the structure

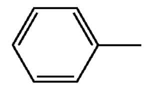

represents toluene.

Other terms are defined in other portions of this description, even though not included in this subsection.

Amide Compounds

In a first aspect, the disclosure provides flavor-modifying compounds, where the flavor-modifying compounds are compounds of formula (I):

(I)

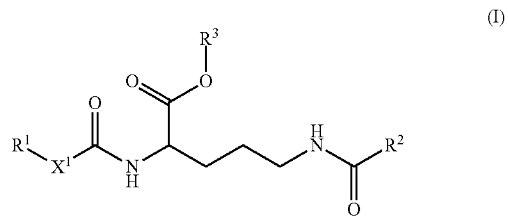

or a comestibly acceptable salt thereof;

wherein:

$R^1$ is $C_{6-14}$ aryl or $C_{4-12}$ heteroaryl, each of which is optionally substituted one or more times by substituents selected independently from the group consisting of $R^Y$;

$R^2$ is a $C_{1-10}$ alkyl, $C_{2-10}$ alkenyl, $C_{6-14}$ aryl, or $C_{1-12}$ heteroaryl, wherein the alkyl and alkenyl groups are each optionally substituted one or more times by substituents selected independently from the group consisting of $R^X$, and wherein the aryl and heteroaryl groups are each optionally substituted one or more times by substituents selected independently from the group consisting of $R^Y$;

$R^3$ is a hydrogen atom or is $C_{1-6}$ alkyl, which is optionally substituted one or more times by —OH, —O—($C_{1-6}$ alkyl), or any combination thereof;

$X^1$ is a direct bond, $C_{1-6}$ alkylene, or $C_{2-6}$ alkenylene, wherein the alkylene and alkenylene groups are each optionally substituted one or more times by substituents selected independently from the group consisting of $R^X$;

$R^X$ is a halogen atom, oxo, —CN, nitro, —OH, —$NH_2$, —C(O)H, —O—C(O)H, —C(O)—OH, —NH—C(O)H, —C(O)—$NH_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, and ($C_{1-6}$ alkoxy)-$C_{1-6}$ alkyl; and $R^Y$ is a halogen atom, oxo, —CN, nitro, —OH, —NH$_2$, —C(O)H, —O—C(O)H, —C(O)—OH, —NH—C(O)H, —C(O)—NH$_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl, $C_{1-6}$ alkyl, and $C_{2-6}$ alkenyl, wherein any adjacent substituents on an aryl or heteroaryl ring can optionally combine to form a fused carbocyclic or heterocyclic ring having from 5 to 7 members.

As used herein, the term "amide compound" or "flavor-modifying compound" refers to compounds of formula (I), or comestibly acceptable salts thereof, as defined above, or any embodiments thereof as set forth below.

In some embodiments, the flavor-modifying compounds can have a particular stereochemistry. Thus, in some embodiments, the flavor-modifying compounds are compounds of formula (Ia)

(Ia)

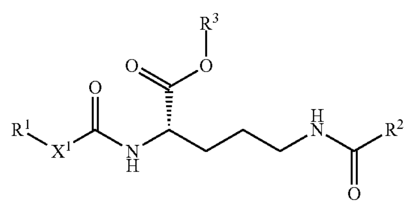

or a comestibly acceptable salt thereof, wherein the values of $R^1$, $R^2$, $R^3$, and $X^1$ are defined in the same was as for compounds of formula (I).

$X^1$ can have any suitable value, according to the definition set forth above. In some embodiments, $X^1$ is a direct bond, such that $R^1$ is connected directly to the adjacent carbonyl carbon. In some other embodiments, $X^1$ is $C_{1-6}$ alkylene. In some further such embodiments, $X^1$ is —CH$_2$—, —CH$_2$—CH$_2$—, or —CH$_2$—CH$_2$—CH$_2$—. In some other embodiments, $X^1$ is $C_{2-6}$ alkenylene. In some such embodiments, $X^1$ is —CH═CH—, in either the Z or E configuration. In some such embodiments, $X^1$ is —CH═CH—, in the Z configuration. In some such embodiments, $X^1$ is —CH═CH—, in the E configuration.

$R^1$ can have any suitable value, according to the definition set forth above. In some embodiments of any of the foregoing embodiments, $R^1$ is phenyl, which is optionally substituted one or more times by substituents selected independently from the group consisting of $R^Y$. In some further such embodiments, $R^1$ is phenyl, which is optionally substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring. In some further such embodiments, $R^1$ is unsubstituted phenyl. In some further such embodiments, $R^1$ is phenyl, which is substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring. In some further such embodiments, $R^1$ is phenyl, which is substituted from one to three times by $C_{1-6}$ alkyl, such as methyl, ethyl, isopropyl, or any combination thereof. In some such embodiments, $R^1$ is phenyl, which is substituted from one to three times by methyl. In some embodiments, $R^1$ is phenyl, which is substituted from one to three times by —OH, —O—($C_{1-6}$ alkyl). In some such embodiments, $R^1$ is phenyl, which is substituted from one to three times by —OH, —O—CH$_3$, —O—CH$_2$—CH$_3$, or any combination thereof. In some embodiments, $R^1$ is 2,3-methylenedioxyphenyl. In some alternate embodiments, $R^1$ is $C_{4-12}$ heteroaryl, such as 2-pyridyl, 3-pyridyl, or 4-pyridyl.

$R^2$ can have any suitable value, according to the definition set forth above. In some embodiments of any of the foregoing embodiments, $R^2$ is phenyl, which is optionally substituted one or more times by substituents selected independently from the group consisting of $R^Y$. In some further such embodiments, $R^2$ is phenyl, which is optionally substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring. In some further such embodiments, $R^2$ is unsubstituted phenyl. In some further such embodiments, $R^2$ is phenyl, which is substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring. In some further such embodiments, $R^2$ is phenyl, which is substituted from one to three times by $C_{1-6}$ alkyl, such as methyl, ethyl, isopropyl, or any combination thereof. In some such embodiments, $R^2$ is phenyl, which is substituted from one to three times by methyl. In some embodiments, $R^2$ is phenyl, which is substituted from one to three times by —OH, —O—($C_{1-6}$ alkyl). In some such embodiments, $R^2$ is phenyl, which is substituted from one to three times by —OH, —O—CH$_3$, —O—CH$_2$—CH$_3$, or any combination thereof. In some further such embodiments, $R^2$ is phenyl, which is substituted one or two times by —OH. In some embodiments, $R^2$ is 2,3-methylenedioxyphenyl. In some alternate embodiments, $R^2$ is $C_{4-12}$ heteroaryl, such as 2-pyridyl, 3-pyridyl, or 4-pyridyl.

In some other embodiments of any of the foregoing embodiments, $R^2$ is $C_{1-10}$ alkyl, which is optionally substituted one or more times by substituents selected independently from the group consisting of $R^X$. In some such embodiments, $R^2$ is $C_{1-10}$ alkyl, which is optionally substituted one or more times by —OH, —O—($C_{1-6}$ alkyl), or any combination thereof. In some further such embodiments, $R^2$ is unsubstituted $C_{1-10}$ alkyl, such as methyl, ethyl, isopropyl, or sec-butyl. In some embodiments, $R^2$ is isopropyl or sec-butyl. In some other such embodiments, $R^2$ is $C_{1-10}$ alkyl, which is substituted one or two times by —OH, such as 4-hydroxybutan-2-yl.

In some other embodiments of any of the foregoing embodiments, $R^2$ is $C_{2-10}$ alkenyl, which is optionally substituted one or more times by substituents selected independently from the group consisting of $R^X$. In some embodiments, $R^2$ is $C_{2-6}$ alkenyl, which is substituted by phenyl, such as (E)-2-phenylethenyl or (Z)-2-phenylethenyl. In some embodiments, $R^2$ is unsubstituted $C_{2-10}$ alkenyl, such as (E)-2-buten-2-yl, (Z)-2-buten-2-yl, (E)-propen-1-yl, (Z)-propen-1-yl, (E)-buten-1-yl, (Z)-buten-1-yl, (E)-3-methylbuten-1-yl, (Z)-3-methylbuten-1-yl, (E)-1-methylpropen1-yl, (Z)-1-methylpropen-1-yl, 2-methylpropenl-yl, 1,2-dimethyl-propen-1-yl, (E)-1-methylbuten1-yl, or (Z)-1-methylbuten-1-yl. In some embodiments, $R^2$ is (E)-2-buten-2-yl. In some embodiments, $R^2$ is (Z)-2-buten-2-yl. In some other embodiments, $R^2$ is $C_{2-10}$ alkenyl, which is substituted once or twice by —OH, such as (E)-4-hydroxybut-2-en-2-yl, (Z)-4-hydroxybut-2-en-2-yl, 3-hydroxybut-1-en-2-yl, or 3,4-dihydroxybut-1-en-2-yl.

$R^3$ can have any suitable value, according to the definition set forth above. In some embodiments, $R^3$ is a hydrogen atom. In some other embodiments, $R^3$ is $C_{1-6}$ alkyl, which is optionally substituted one or more times by —OH, —O—($C_{1-6}$ alkyl), or any combination thereof. In some embodiments, $R^3$ is unsubstituted $C_{1-6}$ alkyl, such as methyl, ethyl, isopropyl, butyl, or the like. In some embodiments, $R^3$ is methyl or ethyl. In some embodiments, $R^3$ is $C_{1-6}$ alkyl, which is substituted one or two times by —OH, —O—$CH_3$, —O—$CH_2$—$CH_3$, or any combination thereof.

Where the compounds disclosed herein have at least one chiral center, they may exist as individual enantiomers and diastereomers or as mixtures of such isomers. In some embodiments in connection with the second aspect, the sweet-enhancing compound has substantial enantiomeric purity.

Separation of the individual isomers or selective synthesis of the individual isomers is accomplished by application of various methods which are well known to practitioners in the art. Unless otherwise indicated (e.g., where the stereochemistry of a chiral center is explicitly shown), all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

The skilled artisan will recognize that some structures described herein may be resonance forms or tautomers of compounds that may be fairly represented by other chemical structures, even when kinetically; the artisan recognizes that such structures may only represent a very small portion of a sample of such compound(s). Such compounds are considered within the scope of the structures depicted, though such resonance forms or tautomers are not represented herein.

Isotopes may be present in the compounds described. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

In some embodiments, the compounds disclosed herein are capable of forming acid and/or base salts by virtue of the presence of amino and/or carboxyl groups or groups similar thereto. Physiologically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Physiologically acceptable salts can be formed using inorganic and organic bases. Inorganic bases from which salts can be derived include, for example, bases that contain sodium, potassium, lithium, ammonium, calcium, magnesium, iron, zinc, copper, manganese, aluminum, and the like; particularly preferred are the ammonium, potassium, sodium, calcium and magnesium salts. In some embodiments, treatment of the compounds disclosed herein with an inorganic base results in loss of a labile hydrogen from the compound to afford the salt form including an inorganic cation such as $Li^+$, $Na^+$, $K^+$, $Mg^{2+}$ and $Ca^{2+}$ and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the salts are comestibly acceptable salts, which are salts suitable for inclusion in comestible food and/or beverage products.

Table 1 provides examples of amide compounds of the present disclosure. In some embodiments, the amide compound is Compound 101 or a comestibly acceptable salt thereof. In some embodiments, the amide compound is Compound 102 or a comestibly acceptable salt thereof. In some embodiments, the amide compound is Compound 103 or a comestibly acceptable salt thereof. In some embodiments, the amide compound is Compound 104 or a comestibly acceptable salt thereof. In some embodiments, the amide compound is Compound 105 or a comestibly acceptable salt thereof. In some embodiments, the amide compound is Compound 106 or a comestibly acceptable salt thereof. In some embodiments, the amide compound is Compound 107 or a comestibly acceptable salt thereof. In some embodiments, the amide compound is Compound 109 or a comestibly acceptable salt thereof. In some embodiments, the amide compound is Compound 109 or a comestibly acceptable salt thereof. In some embodiments, the amide compound is Compound 110 or a comestibly acceptable salt thereof. In some embodiments, the amide compound is Compound 111 or a comestibly acceptable salt thereof. In some embodiments, the amide compound is Compound 112 or a comestibly acceptable salt thereof. In some embodiments, the amide compound is Compound 113 or a comestibly acceptable salt thereof. In some embodiments, the amide compound is Compound 114 or a comestibly acceptable salt thereof. In some embodiments, the amide compound is Compound 115 or a comestibly acceptable salt thereof. In some embodiments, the amide compound is Compound 116 or a comestibly acceptable salt thereof. In some embodiments, the amide compound is Compound 117 or a comestibly acceptable salt thereof. In some embodiments, the amide compound is Compound 118 or a comestibly acceptable salt thereof. In some embodiments, the amide compound is Compound 119 or a comestibly acceptable salt thereof. In some embodiments, the amide compound is Compound 120 or a comestibly acceptable salt thereof. In some embodiments, the amide compound is Compound 121 or a comestibly acceptable salt thereof. In some embodiments, the amide compound is Compound 122 or a comestibly acceptable salt thereof. In some embodiments, the amide compound is Compound 123 or a comestibly acceptable salt thereof. In some embodiments, the amide compound is Compound 124 or a comestibly acceptable salt thereof. In some embodiments, the amide compound is Compound 125 or a comestibly acceptable salt thereof. In some embodiments, the amide compound is Compound 126 or a comestibly acceptable salt thereof. In some embodiments, the amide compound is Compound 127 or a comestibly acceptable salt thereof. In some embodiments, the amide compound is Compound 128 or a comestibly acceptable salt thereof. In some embodiments, the amide compound is Compound 129 or a comestibly acceptable salt thereof. In some embodiments, the amide compound is Compound 130 or a comestibly acceptable salt thereof. In some embodiments, the amide compound is Compound 131 or a comestibly acceptable salt thereof. In some embodiments, the amide compound is Compound 132 or a comestibly acceptable salt thereof. In some embodiments, the amide compound is Compound 133 or a comestibly acceptable salt thereof. In some embodiments, the amide compound is Compound 134 or a comestibly acceptable salt thereof. In some embodiments, the amide compound is Compound 135 or a comestibly acceptable salt thereof. In some embodiments, the amide compound is Compound 136 or a comestibly acceptable salt thereof. In some embodiments, the amide compound is Compound 137 or a comestibly acceptable salt thereof. In some embodiments, the amide compound is Compound 138 or a comestibly acceptable salt thereof. In some embodiments, the amide compound is Compound 139 or a comestibly acceptable salt thereof. In some embodiments, the amide compound is Compound 140 or a comestibly acceptable salt thereof. In some embodiments, the amide compound is Compound 141 or a comestibly acceptable salt thereof. In some embodiments, the amide compound is Compound 142 or a comestibly acceptable salt thereof. In some embodiments, the amide compound is Compound 143 or a comestibly acceptable salt thereof. In some embodiments, the amide compound is Compound 144 or a comestibly acceptable salt thereof. In some embodiments, the amide compound is Compound 145 or a comestibly acceptable salt thereof. In some embodiments, the amide compound is Compound 146 or a comestibly acceptable salt thereof. In some embodiments, the amide compound is Compound 147 or a comestibly acceptable salt thereof. In some embodiments, the amide compound is Compound 148 or a comestibly acceptable salt thereof. In some embodiments, the amide compound is Compound 149 or a comestibly acceptable salt thereof. In some embodiments, the amide compound is Compound 150 or a comestibly acceptable salt thereof. In some embodiments, the amide compound is Compound 151 or a comestibly acceptable salt thereof. In some embodiments, the amide compound is Compound 152 or a comestibly acceptable salt thereof. In some embodiments, the amide compound is Compound 153 or a comestibly acceptable salt thereof. In some embodiments, the amide compound is Compound 154 or a comestibly acceptable salt thereof. In some embodiments, the amide compound is Compound 155 or a comestibly acceptable salt thereof. In some embodiments, the amide compound is Compound 156 or a comestibly acceptable salt thereof. In some embodiments, the amide compound is Compound 157 or a comestibly acceptable salt thereof. In some embodiments, the amide compound is Compound 158 or a comestibly acceptable salt thereof. In some embodiments, the amide compound is Compound 159 or a comestibly acceptable salt thereof. In some embodiments, the amide compound is Compound 160 or a comestibly acceptable salt thereof. In some embodiments, the amide compound is Compound 161 or a comestibly acceptable salt thereof. In some embodiments, the amide compound is Compound 162 or a comestibly acceptable salt thereof. In some embodiments, the amide compound is Compound 163 or a comestibly acceptable salt thereof. In some embodiments, the amide compound is Compound 164 or a comestibly acceptable salt thereof. In some embodiments, the amide compound is Compound 165 or a comestibly acceptable salt thereof. In some embodiments, the amide compound is Compound 166 or a comestibly acceptable salt thereof. In some embodiments, the amide compound is Compound 167 or a comestibly acceptable salt thereof.

TABLE 1

| No. | Structure |
|---|---|
| 101 | 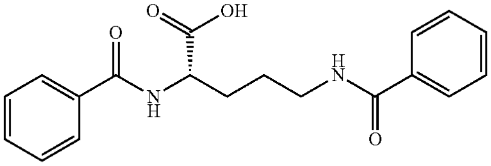 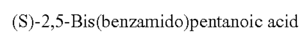 (S)-2,5-Bis(benzamido)pentanoic acid |

TABLE 1-continued

| No. | Structure |
| --- | --- |
| 102 | 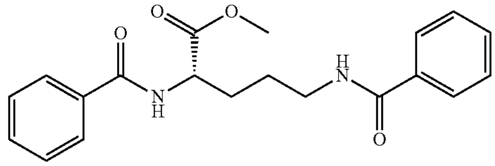<br>Methyl (S)-2,5-bis(benzamido)pentanoate |
| 103 | 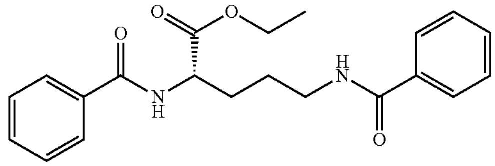<br>Ethyl (S)-2,5-bis(benzamido)pentanoate |
| 104 | 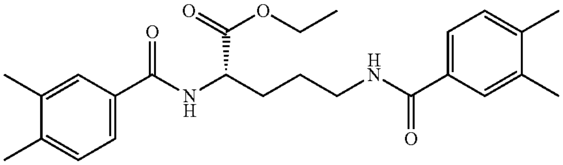<br>Ethyl (S)-5-(3,4-dimethylbenzamido)-2-(4-methylbenzamido)pentanoate |
| 105 | 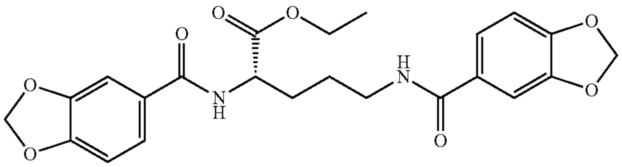<br>Ethyl (S)-2,5-bis(3,4-dimethylbenzamido)pentanoate |
| 106 | 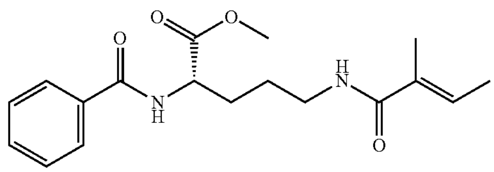<br>Methyl (S,E)-2-benzamido-5-(2-methylbut-2-enamido)pentanoate |
| 107 | 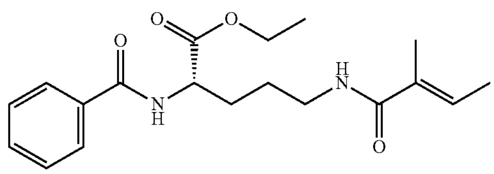<br>Ethyl (S,E)-2-benzamido-5-(2-methylbut-2-enamido)pentanoate |
| 108 | 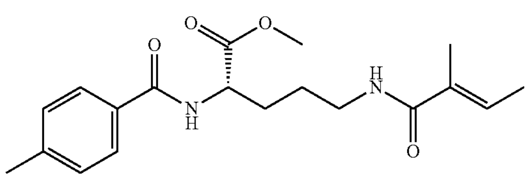<br>Methyl (S,E)-2-(4-methylbenzamido)-5-(2-methylbut-2-enamido)pentanoate |

TABLE 1-continued

| No. | Structure |
| --- | --- |
| 109 | 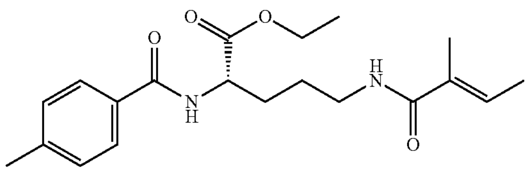<br>Ethyl (S,E)-2-(4-methylbenzamido)-5-(2-methylbut-2-enamido)pentanoate |
| 110 | 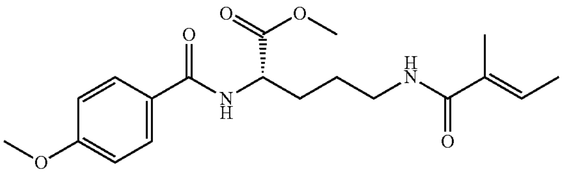<br>Methyl (S,E)-2-(4-methoxybenzamido)-5-(2-methylbut-2-enamido)pentanoate |
| 111 | 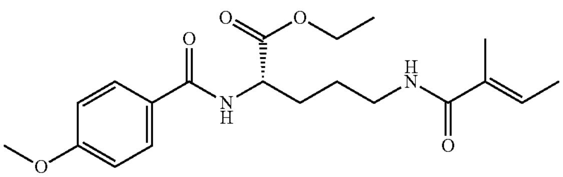<br>Ethyl (S,E)-2-(4-methoxybenzamido)-5-(2-methylbut-2-enamido)pentanoate |
| 112 | 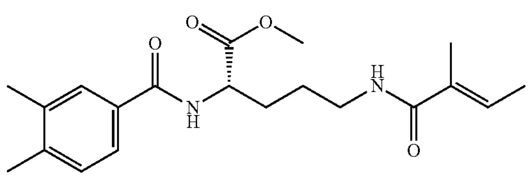<br>Methyl (S,E)-2-(3,4-dimethylbenzamido)-5-(2-methylbut-2-enamido)pentanoate |
| 113 | 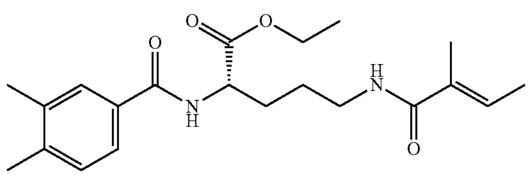<br>Ethyl (S,E)-2-(3,4-dimethylbenzamido)-5-(2-methylbut-2-enamido)pentanoate |
| 114 | 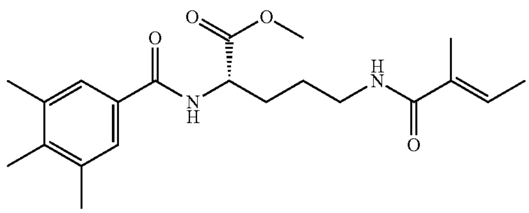<br>Methyl (S,E)-5-(2-methylbut-2-enamido)-2-(3,4,5-trimethylbenzamido)pentanoate |
| 115 | 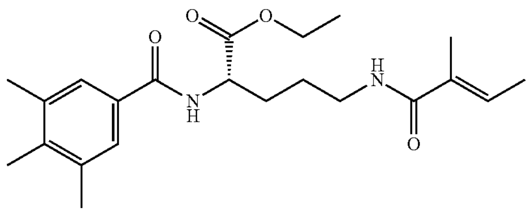<br>Ethyl (S,E)-5-(2-methylbut-2-enamido)-2-(3,4,5-trimethylbenzamido)pentanoate |

TABLE 1-continued

| No. | Structure |
|---|---|
| 116 | 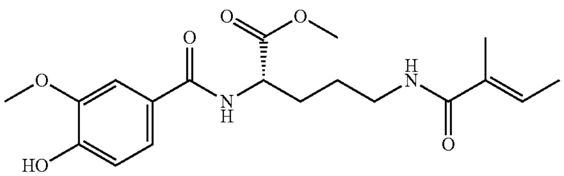<br>Methyl (S,E)-2-(4-hydroxy-3-methoxybenzamido)-5-(2-methylbut-2-enamido)pentanoate |
| 117 | 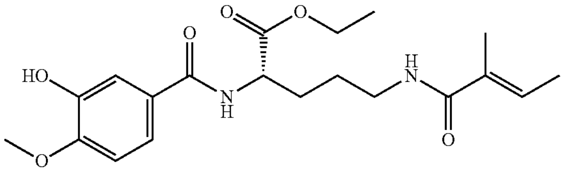<br>Ethyl (S,E)-2-(3-hydroxy-4-methoxybenzamido)-5-(2-methylbut-2-enamido)pentanoate |
| 118 | 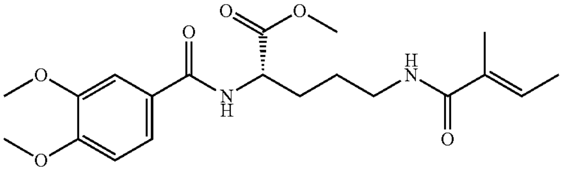<br>Methyl (S,E)-2-(3,4-dimethoxybenzamido)-5-(2-methylbut-2-enamido)pentanoate |
| 119 | 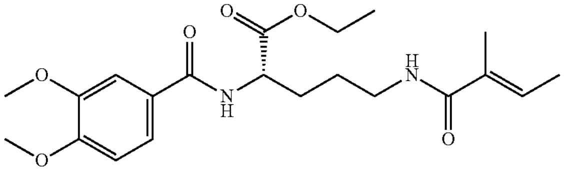<br>Ethyl (S,E)-2-(3,4-dimethoxybenzamido)-5-(2-methylbut-2-enamido)pentanoate |
| 120 | 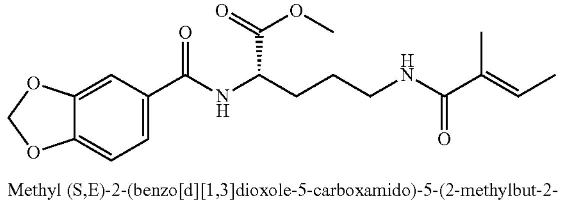<br>Methyl (S,E)-2-(benzo[d][1,3]dioxole-5-carboxamido)-5-(2-methylbut-2-enamido)pentanoate |
| 121 | 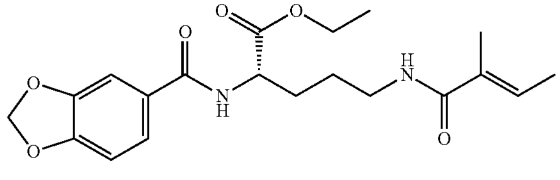<br>Ethyl (S,E)-2-(benzo[d][1,3]dioxole-5-carboxamido)-5-(2-methylbut-2-enamido)pentanoate |
| 122 | 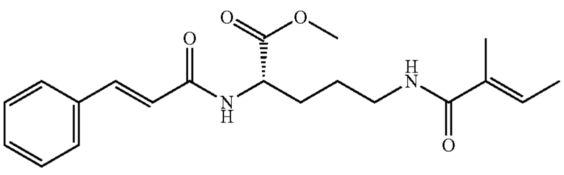<br>Methyl (S)-2-cinnamamido-5-((E)-2-methylbut-2-enamido)pentanoate |

TABLE 1-continued

| No. | Structure |
| --- | --- |
| 123 | 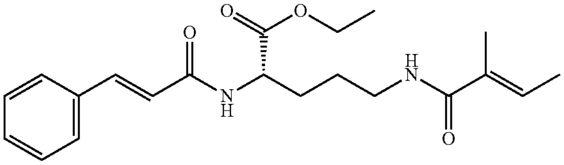 Ethyl (S)-2-cinnamamido-5-((E)-2-methylbut-2-enamido)pentanoate |
| 124 | 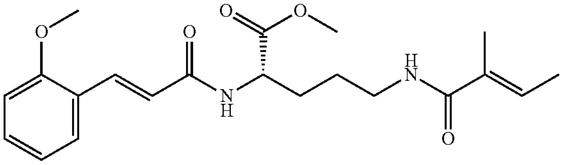 Methyl (S)-2-((E)-3-(2-methoxyphenyl)acrylamido)-5-((E)-2-methylbut-2-enamido)pentanoate |
| 125 | 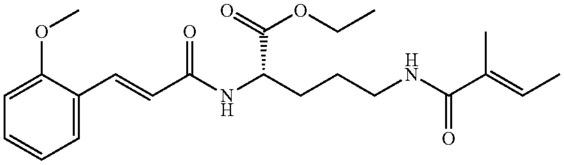 Ethyl (S)-2-((E)-3-(2-methoxyphenyl)acrylamido)-5-((E)-2-methylbut-2-enamido)pentanoate |
| 126 | 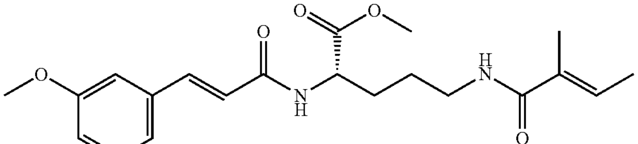 Methyl (S)-2-((E)-3-(3-methoxyphenyl)acrylamido)-5-((E)-2-methylbut-2-enamido)pentanoate |
| 127 | 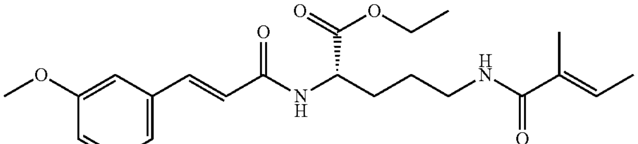 Ethyl (S)-2-((E)-3-(3-methoxyphenyl)acrylamido)-5-((E)-2-methylbut-2-enamido)pentanoate |
| 128 | 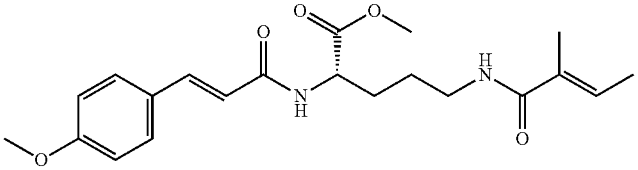 Methyl (S)-2-((E)-3-(4-methoxyphenyl)acrylamido)-5-((E)-2-methylbut-2-enamido)pentanoate |

TABLE 1-continued

| No. | Structure |
|---|---|
| 129 | 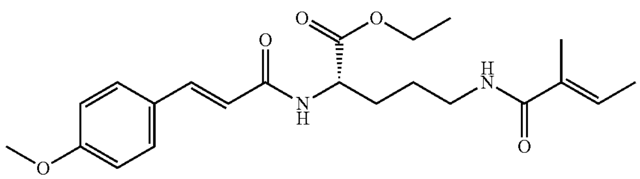<br>Ethyl (S)-2-((E)-3-(4-methoxyphenyl)acrylamido)-5-((E)-2-methylbut-2-enamido)pentanoate |
| 130 | 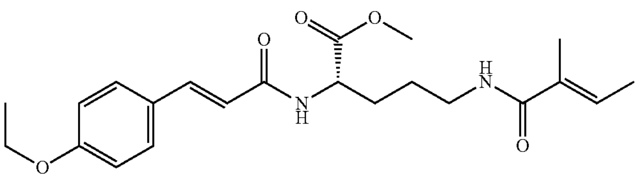<br>Methyl (S)-2-((E)-3-(4-ethoxyphenyl)acrylamido)-5-((E)-2-methylbut-2-enamido)pentanoate |
| 131 | 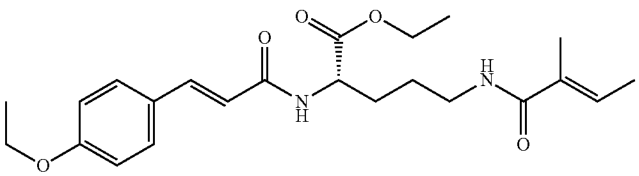<br>Ethyl (S)-2-((E)-3-(4-ethoxyphenyl)acrylamido)-5-((E)-2-methylbut-2-enamido)pentanoate |
| 132 | 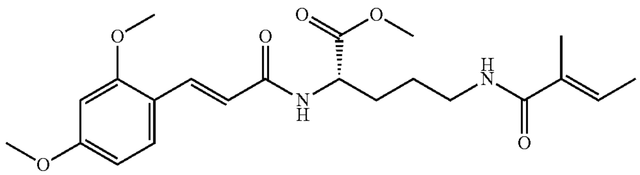<br>Methyl (S)-2-((E)-3-(2,4-dimethoxyphenyl)acrylamido)-5-((E)-2-methylbut-2-enamido)pentanoate |
| 133 | 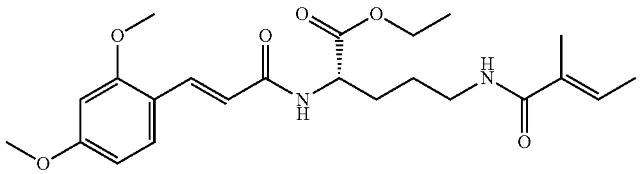<br>Ethyl (S)-2-((E)-3-(2,4-dimethoxyphenyl)acrylamido)-5-((E)-2-methylbut-2-enamido)pentanoate |
| 134 | 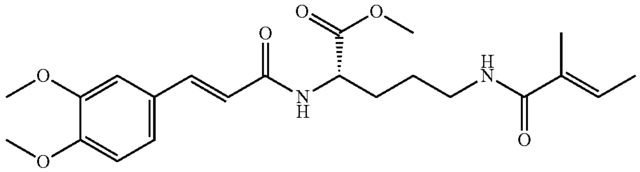<br>Methyl (S)-2-((E)-3-(3,4-dimethoxyphenyl)acrylamido)-5-((E)-2-methylbut-2-enamido)pentanoate |

TABLE 1-continued

| No. | Structure |
| --- | --- |
| 135 | 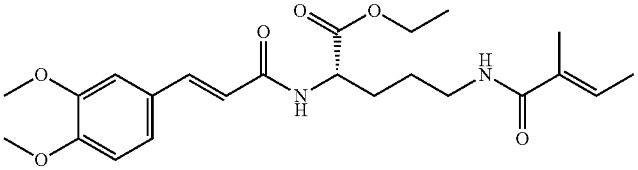 Ethyl (S)-2-((E)-3-(3,4-dimethoxyphenyl)acrylamido)-5-((E)-2-methylbut-2-enamido)pentanoate |
| 136 | 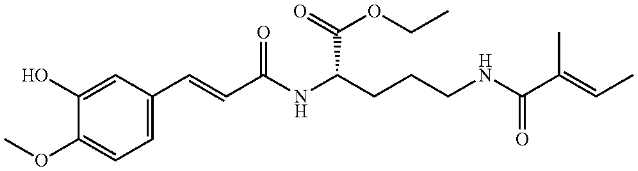 Ethyl (S)-2-((E)-3-(3-hydroxy-4-methoxyphenyl)acrylamido)-5-((E)-2-methylbut-2-enamido)pentanoate |
| 137 | 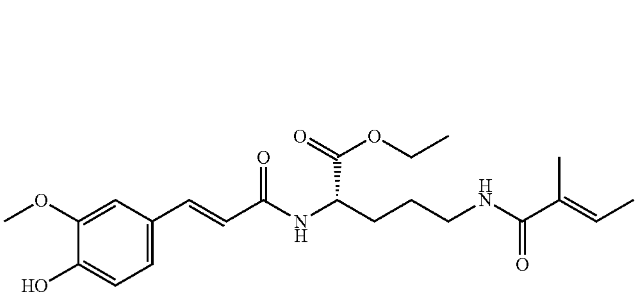 Ethyl (S)-2-((E)-3-(4-hydroxy-3-methoxyphenyl)acrylamido)-5-((E)-2-methylbut-2-enamido)pentanoate |
| 138 | 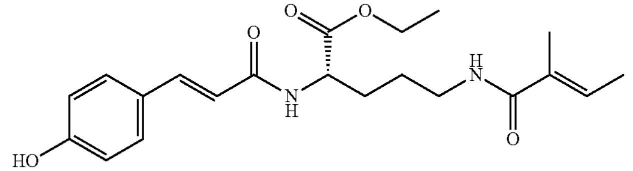 Ethyl (S)-2-((E)-3-(4-hydroxyphenyl)acrylamido)-5-((E)-2-methylbut-2-enamido)pentanoate |
| 139 | 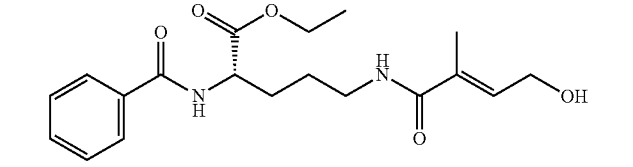 Ethyl (S,E)-2-benzamido-5-(4-hydroxy-2-methylbut-2-enamido)pentanoate |
| 140 | 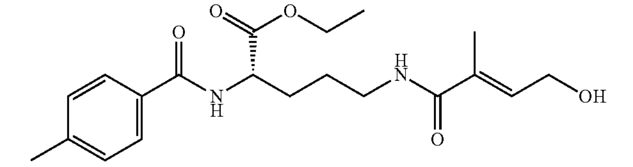 Ethyl (S,E)-5-(4-hydroxy-2-methylbut-2-enamido)-2-(4-methylbenzamido)pentanoate |

TABLE 1-continued

| No. | Structure |
|---|---|
| 141 | 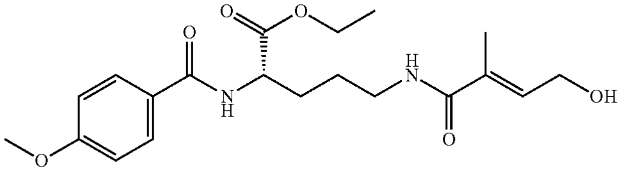<br>Ethyl (S,E)-5-(4-hydroxy-2-methylbut-2-enamido)-2-(4-methoxybenzamido)pentanoate |
| 142 | 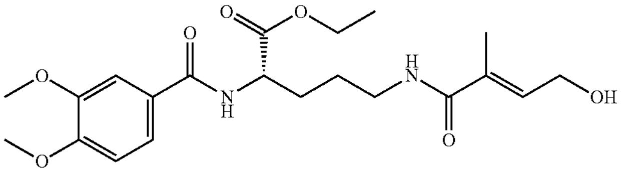<br>Ethyl (S,E)-2-(3,4-dimethoxybenzamido)-5-(4-hydroxy-2-methylbut-2-enamido)pentanoate |
| 143 | 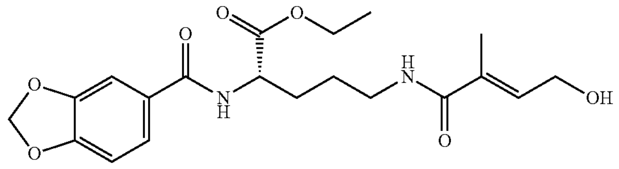<br>Ethyl (S,E)-2-(benzo[d][1,3]dioxole-5-carboxamido)-5-(4-hydroxy-2-methylbut-2-enamido)pentanoate |
| 144 | 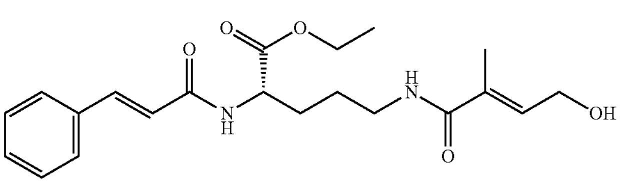<br>Ethyl (S)-2-cinnamamido-5-((E)-4-hydroxy-2-methylbut-2-enamido)pentanoate |
| 145 | 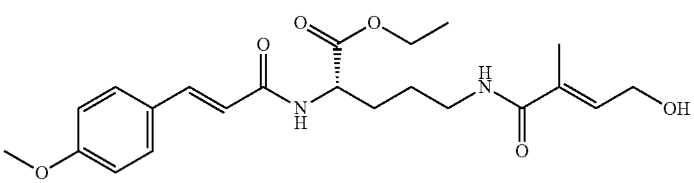<br>Ethyl (S)-5-((E)-4-hydroxy-2-methylbut-2-enamido)-2-((E)-3-(4-methoxyphenyl)acrylamido)pentanoate |
| 146 | 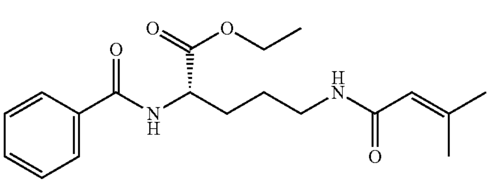<br>Ethyl (S)-2-benzamido-5-(3-methylbut-2-enamido)pentanoate |
| 147 | 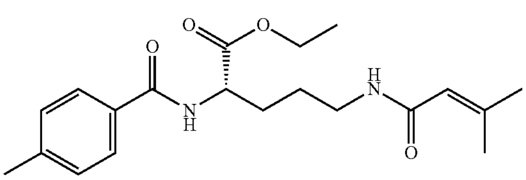<br>Ethyl (S)-2-(4-methylbenzamido)-5-(3-methylbut-2-enamido)pentanoate |

TABLE 1-continued

| No. | Structure |
|---|---|
| 148 | 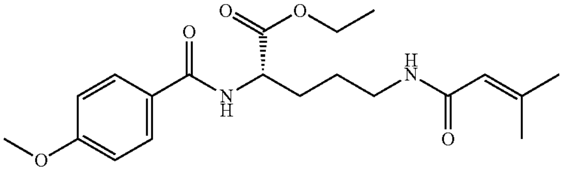 Ethyl (S)-2-(4-methoxybenzamido)-5-(3-methylbut-2-enamido)pentanoate |
| 149 | 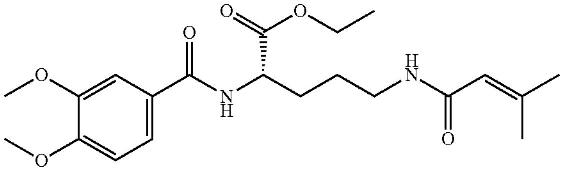 Ethyl (S)-2-(3,4-dimethoxybenzamido)-5-(3-methylbut-2-enamido)pentanoate |
| 151 | 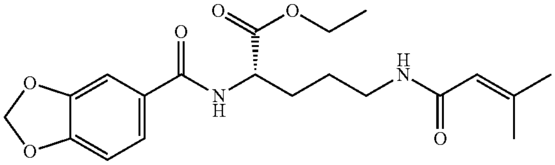 Ethyl (S)-2-(benzo[d][1,3]dioxole-5-carboxamido)-5-(3-methylbut-2-enamido)pentanoate |
| 152 | 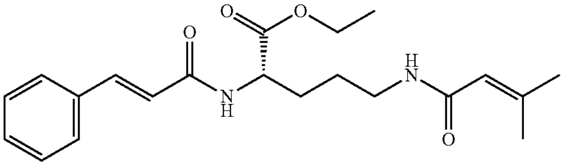 Ethyl (S)-2-cinnamamido-5-(3-methylbut-2-enamido)pentanoate |
| 153 | 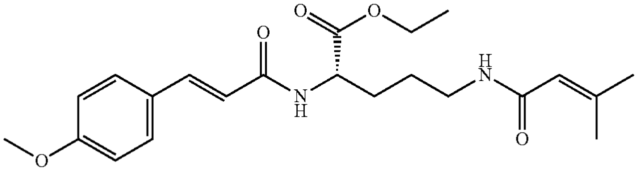 Ethyl (S,E)-2-(3-(4-methoxyphenyl)acrylamido)-5-(3-methylbut-2-enamido)pentanoate |
| 154 | 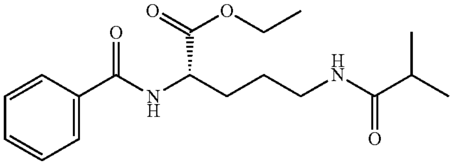 Ethyl (S)-2-benzamido-5-isobutyramidopentanoate |
| 155 | 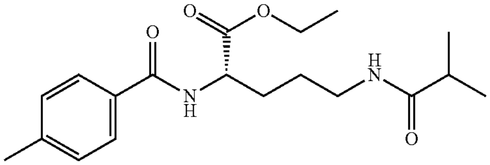 Ethyl (S)-5-isobutyramido-2-(4-methylbenzamido)pentanoate |

TABLE 1-continued

| No. | Structure |
| --- | --- |
| 156 | 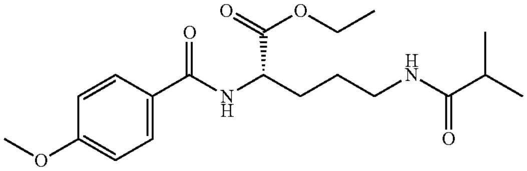 Ethyl (S)-5-isobutyramido-2-(4-methoxybenzamido)pentanoate |
| 157 | 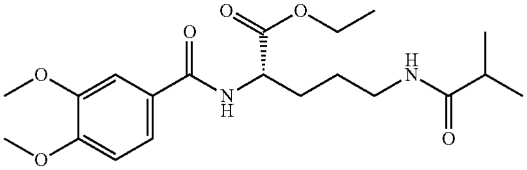 Ethyl (S)-2-(3,4-dimethoxybenzamido)-5-isobutyramidopentanoate |
| 158 | 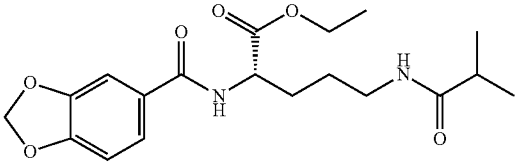 Ethyl (S)-2-(benzo[d][1,3]dioxole-5-carboxamido)-5-isobutyramidopentanoate |
| 159 | 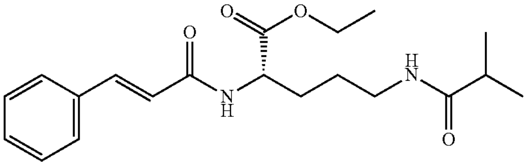 Ethyl (S)-2-cinnamamido-5-isobutyramidopentanoate |
| 160 | 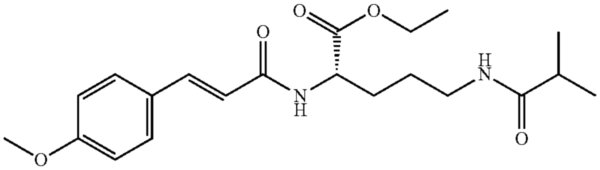 Ethyl (S,E)-5-isobutyramido-2-(3-(4-methoxyphenyl)acrylamido)pentanoate |
| 161 | 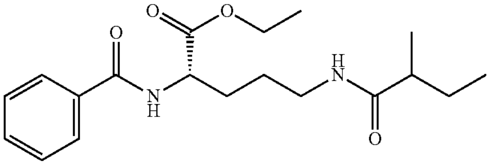 Ethyl (2S)-2-benzamido-5-(2-methylbutanamido)pentanoate |
| 162 | 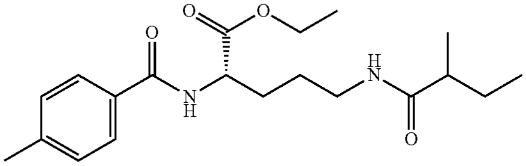 Ethyl (2S)-2-(4-methylbenzamido)-5-(2-methylbutanamido)pentanoate |

TABLE 1-continued

| No. | Structure |
|---|---|
| 163 | 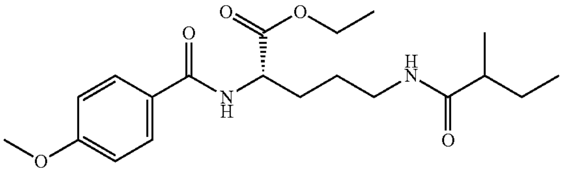<br>Ethyl (2S)-2-(4-methoxybenzamido)-5-(2-methylbutanamido)pentanoate |
| 164 | 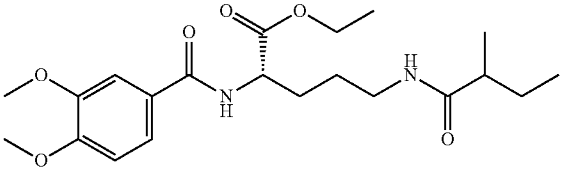<br>Ethyl (2S)-2-(3,4-dimethoxybenzamido)-5-(2-methylbutanamido)pentanoate |
| 165 | 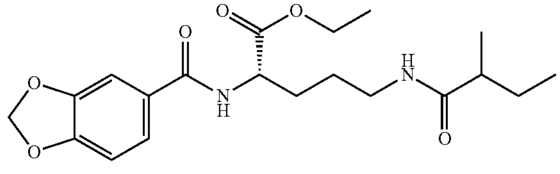<br>Ethyl (2S)-2-(benzo[d][1,3]dioxole-5-carboxamido)-5-(2-methylbutanamido)pentanoate |
| 166 | 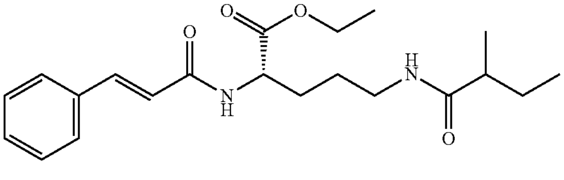<br>Ethyl (2S)-2-cinnamamido-5-(2-methylbutanamido)pentanoate |
| 167 | 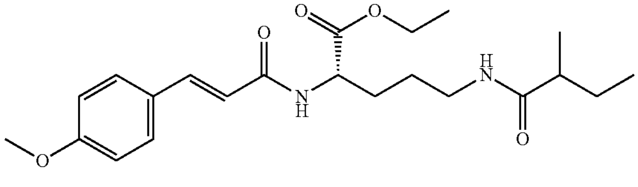<br>Ethyl (2S)-2-((E)-3-(4-methoxyphenyl)acrylamido)-5-(2-methylbutanamido)pentanoate |

In some embodiments, the amide compounds exist as a free acid or a free base. In some embodiments, the amide compound is Compound 101. In some embodiments, the amide compound is Compound 102. In some embodiments, the amide compound is Compound 103. In some embodiments, the amide compound is Compound 104. In some embodiments, the amide compound is Compound 105. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133. In some embodiments, the amide compound is Compound 134. In some embodiments, the amide compound is Compound 135. In some embodiments, the amide compound is Compound 136. In some embodiments, the amide compound is Compound 137. In some embodiments, the amide compound is Compound 138. In some embodiments, the amide compound is Compound 139. In some embodiments, the amide compound is Compound 140. In some embodiments, the amide compound is Compound 141. In some embodiments, the amide compound is Compound 142. In some embodiments, the amide compound is Compound 143. In some embodiments, the amide compound is Compound 144. In some embodiments, the amide compound is Compound 145. In some embodiments, the amide compound is Compound 146. In some embodiments, the amide compound is Compound 147. In some embodiments, the amide compound is Compound 148. In some embodiments, the amide compound is Compound 149. In some embodiments, the amide compound is Compound 150. In some embodiments, the amide compound is Compound 151. In some embodiments, the amide compound is Compound 152. In some embodiments, the amide compound is Compound 153. In some embodiments, the amide compound is Compound 154. In some embodiments, the amide compound is Compound 155. In some embodiments, the amide compound is Compound 156. In some embodiments, the amide compound is Compound 157. In some embodiments, the amide compound is Compound 158. In some embodiments, the amide compound is Compound 159. In some embodiments, the amide compound is Compound 160. In some embodiments, the amide compound is Compound 161. In some embodiments, the amide compound is Compound 162. In some embodiments, the amide compound is Compound 163. In some embodiments, the amide compound is Compound 164. In some embodiments, the amide compound is Compound 165. In some embodiments, the amide compound is Compound 166. In some embodiments, the amide compound is Compound 167.

Solid State Forms and Solutions of Flavor-Modifying Compounds

In another aspect, the disclosure provides various solid-state forms of the amide compounds (i.e., the flavor-modifying compounds).

In some embodiments, the amide compounds exists as a crystalline solid, either in substantially pure form or in a formulation such as those set forth below. The crystalline solid can have any suitable polymorphic form, such as any polymorphic form obtainable via recrystallization in any suitable solvent system, according to techniques commonly used in the art of polymorph screening.

In some other embodiments, the amide compounds exists as an amorphous solid or a semi-amorphous solid, meaning that it lacks any regular crystalline structure. Such solids can be generated using standard techniques, such as spray drying, and the like.

In some embodiments, the amide compounds exists as a solvate, which is a pseudomorphic form of the compound in which one or more solvent molecules (such as water molecules) are taken up into the crystalline structure. Any suitable solvent or combination of solvents can be used, including, but not limited to, water, methanol, ethanol, n-propanol, isopropanol, n-butanol, 2-butanol, isobutanol, ethyl acetate, ethylene glycol, 1,2-propylene glycol, 1,3-propylene glycol, and the like. In some embodiments, the disclosure provides hydrates of the amide compounds. Such solvates can be generated by any suitable means, such as those techniques typically used by skilled artisans in the field of polymorph and solvate screening.

In some other embodiments, the compounds exist as a co-crystal with one or more other compounds, such as one or more other sweetener compounds. The amide compounds can form a co-crystal with any suitable compound. Non-limiting examples of such suitable compounds include purine ribonucleotides (such as inosine monophosphate (IMP) and guanosine monophosphate (GMP)), an arginate, a glutamate, a gamma-glutamyl-containing oligopeptide (such as gamma-glutamyl-containing tripeptides);

In some embodiments, the amide compounds is in the form of a dry particle. Such dry particles can be formed by standard techniques in the art, such as dry granulation, wet granulation, and the like. Such particles can also contain a number of excipients, including, inert diluents, such as calcium carbonate, sodium carbonate, lactose, calcium phosphate, and sodium phosphate; granulating and disintegrating agents, such as starch, cellulosic materials, and alginic acid; binding agents, such as gelatin, guar gum, and acacia; and lubricating agents, such as magnesium stearate, stearic acid, and talc. Other excipients typically used in food and beverage products can also be included, such as typical foodstuff materials.

In some embodiments, the amide compounds are in the form of a liquid solution or a liquid suspension. Such compositions can also include: carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. Such compositions can also include one or more coloring agents, one or more flavoring agents, and the like. Such liquid suspensions and solutions have a liquid carrier. In general, the liquid carrier comprises water. In some such cases, the liquid composition is an emulsion, such as an oil-in-water or a water-in-oil emulsion. Further, in some cases, water may be too polar to dissolve the amide compounds to the desired concentration. In such instances, it can be desirable to introduce water-miscible solvents, such as alcohols, glycols, polyols, and the like, to the solvent to enhance solubilization of the amide compounds.

In some embodiments, the amide compounds, is in the form of a solution, i.e., are solvated within a liquid carrier. In some embodiments, the liquid carrier is an aqueous carrier. In some such embodiments, the solutions comprise a comestibly acceptable salt of an amide compound, such as a hydrochloride salt, a potassium salt, or a sodium salt. Such solutions can be diluted to any suitable concentration.

Uses and Methods

In certain aspects, the disclosure provides uses and methods of using the amide compounds (in any form according to the preceding aspects and embodiments thereof).

In certain aspects, the disclosure provides uses of an amide compound (according to any of the embodiments set forth above). In some embodiments, the use comprises modifying a flavor of an ingestible composition, such as a food or beverage product. In related aspects, the disclosure provides corresponding methods of using an amide compound (according to any of the embodiments set forth above), comprising introducing the amide compound to an ingestible composition. In some embodiments, the ingestible composition is a flavored product such as a flavored food or beverage product. Such ingestible compositions can have any suitable form or contain any suitable additional ingredients, according to the embodiments set forth below. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) for modifying a flavor of an ingestible composition. In a related aspect, the disclosure provides corresponding methods of modifying a flavor of an ingestible composition, the method comprising introducing an amide compound (according to any of the embodiments set forth above) to an ingestible composition. In some embodiments, the ingestible composition is a flavored product such as a flavored food or beverage product. Such ingestible compositions can have any suitable form or contain any suitable additional ingredients, according to the embodiments set forth below. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to enhance a salty taste of an ingestible composition. In related aspects, the disclosure provides uses of an amide compound (according to any of the embodiments set forth above) to reduce the salt (e.g., sodium chloride) content of an ingestible composition. In some embodiments, the presence of the amide compound in the ingestible composition allows one to reduce the concentration of salt (for example, sodium chloride) in the ingestible composition by from 5% to 20%, or from 5% to 30%, or from 5% to 40%, or from 5% to 50%, or from 5% to 60%, or from 5% to 70%, or from 5% to 80%, or from 5% to 90%, and have a composition that has a similar perceived salt content to a comparable composition without the amide compound and a standard concentration of salt. In a related aspect, the disclosure provides corresponding methods of enhancing a salty taste of an ingestible composition, the method comprising introducing an amide compound (according to any of the embodiments set forth above) to an ingestible composition. Such ingestible compositions can have any suitable form or contain any suitable additional ingredients, according to the embodiments set forth below. In some embodiments of these aspects, the ingestible composition comprises sodium chloride, potassium chloride, or any combination thereof. In some embodiments, the ingestible composition comprises sodium chloride. In some embodiments, the ingestible composition is a flavored product such as a flavored food or beverage product. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound pound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to enhance an umami taste of an ingestible composition. In related aspects, the disclosure provides uses of an amide compound (according to any of the embodiments set forth above) to reduce or eliminate the glutamate content of an ingestible composition. In a related aspect, the disclosure provides corresponding methods of enhancing an umami taste of an ingestible composition, the method comprising introducing an amide compound (according to any of the embodiments set forth above) to an ingestible composition. Such ingestible compositions can have any suitable form or contain any suitable additional ingredients, according to the embodiments set forth below. In some embodiments of these aspects, the ingestible composition is free or substantially free (for example, no more than 1000 ppm) of monosodium glutamate (MSG). In some embodiments, the presence of the amide compound in the ingestible composition allows one to reduce the concentration of glutamate in the ingestible composition by from 5% to 20%, or from 5% to 30%, or from 5% to 40%, or from 5% to 50%, or from 5% to 60%, or from 5% to 70%, or from 5% to 80%, or from 5% to 90%, and have a composition that has a similar perceived glutamate content to a comparable composition without the amide compound and a standard concentration of glutamate. In some embodiments, the ingestible composition comprises a purinic ribonucleotide, such as inosine monophosphate (IMP), guanosine monophosphate (GMP), hypoxanthine, inosine, or any combination thereof. In some embodiments, the ingestible composition is a flavored product such as a flavored food or beverage product. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to enhance a kokumi taste of an ingestible composition. In related aspects, the disclosure provides uses of an amide compound (according to any of the embodiments set forth above) to reduce or eliminate the gamma-glutamyl-containing oligopeptide content of an ingestible composition. In related aspects, the disclosure provides uses of an amide compound (according to any of the embodiments set forth above) to reduce or eliminate the animal content (e.g., animal broth, meat, etc.) of an ingestible composition. In a related aspect, the disclosure provides corresponding methods of enhancing a kokumi taste of an ingestible composition, the method comprising introducing an amide compound (according to any of the embodiments set forth above) to an ingestible composition. Such ingestible compositions can have any suitable form or contain any suitable additional ingredients, according to the embodiments set forth below. In some embodiments of these aspects, the ingestible composition is free or substantially free (for example, no more than 1000 ppm) of gamma-glutamyl-containing oligopeptides, such as gamma-glutamyl-containing tripeptides. In some embodiments, the presence of the amide compound in the ingestible composition allows one to reduce the concentration of gamma-glutamyl tripeptides in the ingestible composition by from 5% to 20%, or from 5% to 30%, or from 5% to 40%, or from 5% to 50%, or from 5% to 60%, or from 5% to 70%, or from 5% to 80%, or from 5% to 90%, and have a composition that has a similar perceived gamma-glutamyl tripeptide content to a comparable composition without the amide compound and a standard concentration of gamma-glutamyl tripeptides. In some embodiments, the ingestible composition comprises one or more gamma-glutamyl peptides, such as one or more gamma-glutamyl tripeptides. In some embodiments, the ingestible composition is a flavored product such as a flavored food or beverage product. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to enhance a perceived juiciness of an ingestible composition. In a related aspect, the disclosure provides corresponding methods of enhancing a perceived juiciness of a comestible composition comprising introducing an amide compound (according to any of the embodiments set forth above) to an ingestible composition. Such ingestible compositions can have any suitable form or contain any suitable additional ingredients, according to the embodiments set forth below. In some embodiments, the ingestible composition is a flavored product such as a flavored food or beverage product, such as a meat or dairy analogue product. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to enhance a perceived fattiness of an ingestible composition. In a related aspect, the disclosure provides corresponding methods of enhancing a perceived fattiness of a comestible composition comprising introducing an amide compound (according to any of the embodiments set forth above) to an ingestible composition. In certain related aspects, the disclosure provides uses of an amide compound (according to any of the embodiments set forth above) to reduce the fat content of an ingestible composition. In some embodiments, the presence of the amide compound in the ingestible composition allows one to reduce the concentration of fat in the ingestible composition by from 5% to 20%, or from 5% to 30%, or from 5% to 40%, or from 5% to 50%, or from 5% to 60%, or from 5% to 70%, or from 5% to 80%, or from 5% to 90%, and have a composition that has a similar perceived fat content to a comparable composition without the amide compound and a standard concentration of fat. Such ingestible compositions can have any suitable form or contain any suitable additional ingredients, according to the embodiments set forth below. In some embodiments, the ingestible composition is a flavored product such as a flavored food or beverage product, such as a meat or dairy analogue product. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

In certain aspects, the disclosure provides uses of an amide compound (according to any of the embodiments set forth above) to reduce an amount of alcohol in an ingestible composition. In related aspects, the disclosure provides methods of reducing an amount of alcohol in an ingestible composition, the method comprising introducing an amide compound (according to any of the embodiments set forth above) to an ingestible composition. In some embodiments, the ingestible composition is a beverage product, such as a low-alcohol or alcohol-free beverage product, including, but not limited to, a low-alcohol beer, an alcohol-free beer, a low-alcohol flavored seltzer beverage, or an alcohol-free seltzer beverage. In other embodiments, the comestible product is a food product, such as a confectionary product or a candy product. In some embodiments, the presence of the amide compound in the ingestible composition allows one to reduce the concentration of alcohol in the ingestible composition by from 5% to 20%, or from 5% to 30%, or from 5% to 40%, or from 5% to 50%, or from 5% to 60%, or from 5% to 70%, or from 5% to 80%, or from 5% to 90%, and have a composition that has a similar perceived alcoholic content to a comparable composition without the amide compound and a standard concentration of alcohol. In some embodiments, the presence of the amide compound in the ingestible composition allows one to eliminate entirely or substantially eliminate (for example, reduce by at least 95%, or by at least 97%, or by at least 99%) alcohol, and have a product that has a similar perceived alcoholic content to a comparable product without the amide compound and a standard concentration of alcohol. In some embodiments, the amide compound is Compound 103. In some embodiments, the amide compound is Compound 106. In some embodiments, the amide compound is Compound 107. In some embodiments, the amide compound is Compound 108. In some embodiments, the amide compound is Compound 109. In some embodiments, the amide compound is Compound 110. In some embodiments, the amide compound is Compound 111. In some embodiments, the amide compound is Compound 112. In some embodiments, the amide compound is Compound 113. In some embodiments, the amide compound is Compound 114. In some embodiments, the amide compound is Compound 115. In some embodiments, the amide compound is Compound 116. In some embodiments, the amide compound is Compound 117. In some embodiments, the amide compound is Compound 118. In some embodiments, the amide compound is Compound 119. In some embodiments, the amide compound is Compound 120. In some embodiments, the amide compound is Compound 121. In some embodiments, the amide compound is Compound 122. In some embodiments, the amide compound is Compound 123. In some embodiments, the amide compound is Compound 124. In some embodiments, the amide compound is Compound 125. In some embodiments, the amide compound is Compound 126. In some embodiments, the amide compound is Compound 127. In some embodiments, the amide compound is Compound 128. In some embodiments, the amide compound is Compound 129. In some embodiments, the amide compound is Compound 130. In some embodiments, the amide compound is Compound 131. In some embodiments, the amide compound is Compound 132. In some embodiments, the amide compound is Compound 133.

Ingestible Compositions

The foregoing uses and methods generally involve the use or introduction of the amide compound to an ingestible composition having one or more additional components or ingredients. For example, in at least one aspect, the disclosure provides ingestible compositions comprising any amide compounds of the foregoing aspects.

The ingestible compositions can include the amide compounds (according to any of the embodiments set forth above) in any suitable concentration. In some embodiments, the amide compounds are present in an amount sufficient to enhance a taste (e.g., enhance an umami, enhance a kokumi, or enhance a salty taste of the ingestible composition. Thus, in some embodiments, the ingestible composition comprises the amide compounds in a concentration of no greater than 1000 ppm, or no greater than 900 ppm, or no greater than 800 ppm, or no greater than 700 ppm, or no greater than 600 ppm, or no greater than 500 ppm, or no greater than 400 ppm, or no greater than 300 ppm, or no greater than 200 ppm, or no greater than 150 ppm, or no greater than 100 ppm, or no greater than 50 ppm, or no greater than 40 ppm, or no greater than 30 ppm, or no greater than 20 ppm, or no greater than 10 ppm. In some embodiments, the amide compound is present in a minimum amount, such as 0.1 ppm, 0.5 ppm, or 1 ppm. Thus, in some embodiments, the ingestible composition comprises the amide compound in a concentration ranging from 1 ppm to 1000 ppm, or 1 ppm to 900 ppm, or 1 ppm to 800 ppm, or 1 ppm to 700 ppm, or 1 ppm to 600 ppm, or 1 ppm to 500 ppm, or 1 ppm to 400 ppm, or 1 ppm to 300 ppm, or 1 ppm to 200 ppm, or from 1 ppm to 150 ppm, or from 1 ppm to 100 ppm, or from 1 ppm to 50 ppm, or from 1 ppm to 40 ppm, or from 1 ppm to 30 ppm, or from 1 ppm to 20 ppm, or from 0.5 ppm to 1000 ppm, or from 0.5 ppm to 900 ppm, or from 0.5 ppm to 800 ppm, or from 0.5 ppm to 700 ppm, or from 0.5 ppm to 600 ppm, or from 0.5 ppm to 500 ppm, or from 0.5 ppm to 400 ppm, or from 0.5 ppm to 300 ppm, or from 0.5 ppm to 200 ppm, or from 0.5 ppm to 150 ppm, or from 0.5 ppm to 100 ppm, or from 0.5 ppm to 50 ppm, or from 0.5 ppm to 40 ppm, or from 0.5 ppm to 30 ppm, or from 0.5 ppm to 20 ppm, or from 0.1 ppm to 1000 ppm, or from 0.1 ppm to 900 ppm, or from 0.1 ppm to 800 ppm, or from 0.1 ppm to 700 ppm, or from 0.1 ppm to 600 ppm, or from 0.1 ppm to 500 ppm, or from 0.1 ppm to 400 ppm, or from 0.1 ppm to 300 ppm, or from 0.1 ppm to 200 ppm, or from 0.1 ppm to 150 ppm, or from 0.1 ppm to 100 ppm, or from 0.1 ppm to 50 ppm, or from 0.1 ppm to 40 ppm, or from 0.1 ppm to 30 ppm, or from 0.1 ppm to 20 ppm.

In some embodiments of any of the foregoing embodiments, the ingestible composition comprises a salty tastant and an amide compound (according to any of the embodiments set forth above). In some embodiments, the salty tastant is sodium chloride, potassium chloride, or a combination thereof. In some such embodiments, the salty tastant is sodium chloride. In some other embodiments, the salty tastant is potassium chloride. In some embodiments, the ingestible composition comprises the salty tastant at a lower concentration than an equally salty-tasting composition not comprising the amide compound (according to any of the embodiments set forth above). In some such embodiments, the concentration of the salty tastants is more than 10% less, more than 20% less, more than 30% less, more than 40% less, more than 50% less, more than 60% less, or more than 70% less, or more than 80% less, or more than 90% less than the concentration of salty tastants in an equally salty-tasting composition not comprising the amide compound (according to any of the embodiments set forth above). In some embodiments, the salty tastant is present in the ingestible composition at a concentration ranging from 0.001 percent by weight to 1.0 percent by weight, or from 0.001 percent by weight to 0.9 percent by weight, or from 0.001 percent by weight to 0.8 percent by weight, or from 0.001 percent by weight to 0.7 percent by weight, or from 0.001 percent by weight to 0.6 percent by weight, or from 0.001 percent by weight to 0.5 percent by weight, or from 0.001 percent by weight to 0.4 percent by weight, or from 0.001 percent by weight to 0.3 percent by weight, or from 0.001 percent by weight to 0.2 percent by weight, or from 0.001 percent by weight to 0.1 percent by weight, or from 0.01 percent by weight to 1.0 percent by weight, or from 0.01 percent by weight to 0.9 percent by weight, or from 0.01 percent by weight to 0.8 percent by weight, or from 0.01 percent by weight to 0.7 percent by weight, or from 0.01 percent by weight to 0.6 percent by weight, or from 0.01 percent by weight to 0.5 percent by weight, or from 0.01 percent by weight to 0.4 percent by weight, or from 0.01 percent by weight to 0.3 percent by weight, or from 0.01 percent by weight to 0.2 percent by weight, or from 0.01 percent by weight to 0.1 percent by weight, based on the total weight of the ingestible composition.

In some embodiments of any of the foregoing embodiments, the ingestible composition comprises an umami tastant and the amide compound (according to any of the embodiments set forth above). In some embodiments, the umami tastant is a glutamate, an arginate, a purine ribonucleitide, or a combination thereof. In some such embodiments, the salty tastant is monosodium glutamate (MSG). In some embodiments, the umami tastant is a purine ribonucleotide (for example, inosine monophosphate (IMP), guanosine monophosphate (GMP), hypoxanthine, inosine, or any combination thereof. In some embodiments, the umami tastant is inosine monophosphate (IMP), guanosine monophosphate (GMP), or a combination thereof. In some embodiments, the ingestible composition comprises the umami tastant at a lower concentration than an equally umami-tasting composition not comprising the amide compound (according to any of the embodiments set forth above). In some such embodiments, the concentration of the umami tastants is more than 10% less, more than 20% less, more than 30% less, more than 40% less, more than 50% less, more than 60% less, or more than 70% less, or more than 80% less, or more than 90% less than the concentration of umami tastants in an equally umami-tasting composition not comprising the amide compound (according to any of the embodiments set forth above). In some embodiments, the umami tastant is present in the ingestible composition at a concentration ranging from 1 ppm to 1000 ppm, or from 1 ppm to 900 ppm, or from 1 ppm to 800 ppm, or from 1 ppm to 700 ppm, or from 1 ppm to 600 ppm, or from 1 ppm to 500 ppm, or from 1 ppm to 400 ppm, or from 1 ppm to 300 ppm, or from 1 ppm to 200 ppm, or from 1 ppm to 100 ppm, or from 1 ppm to 75 ppm, or from 1 ppm to 50 ppm, or from 1 ppm to 25 ppm, or from 1 ppm to 10 ppm, based on the total weight of the ingestible composition. In some embodiments where the umami tastant is monosodium glutamate, the ingestible composition comprises no more than 10 ppm, or no more than 5 ppm, or no more than 1 ppm of monosodium glutamate, based on the total weight of the ingestible composition.

In certain particular embodiments, the ingestible composition comprises fat, such as animal or vegetable fat, and an amide compound (according to any of the embodiments set forth above). In some such embodiments, the introduction of the amide compound permits one to use less fat (such as more than 10% less, more than 20% less, more than 30% less, more than 40% less, more than 50% less, more than 60% less, or more than 70% less, or more than 80% less, or more than 90% less) and still achieve a level of fatty characteristic of a comparable product that employs a higher concentration of fat but not the amide compound. In some related embodiments, the use of the amide compound, permits the elimination of fat from the composition. The fat can be any suitable fat, such as a fat derived from an animal or vegetable fat. In some embodiments, the fat is an animal fat, such as milk fat (including fat in various cheeses), beef fat, pork fat, poultry fat, lamb fat, goat fat, fish oil, butter, and the like. In some other embodiments, the fat is a non-animal fat, such as olive oil, canola oil, corn oil, safflower oil, nut oil, peanut oil, cashew oil, soybean oil, palm oil, palm kernel oil, coconut oil, cocoa butter, and nut butters (such as peanut butter, cashew butter, almond butter, hazelnut butter, and the like). In some embodiments, the fat is cocoa butter. The fat can be present in any suitable concentration in the ingestible composition. In some embodiments, the fat concentration in the ingestible composition ranges from 1 percent by weight to 60 percent by weight, or from 1 percent by weight to 50 percent by weight, or from 1 percent by weight to 40 percent by weight, or from 1 percent by weight to 30 percent by weight, or from 1 percent by weight to 20 percent by weight, or from 1 percent by weight to 10 percent by weight.

In some embodiments of any of the foregoing embodiments, the ingestible composition comprises a kokumi tastant and the amide compound (according to any of the embodiments set forth above). In some embodiments, the kokumi tastant is a yeast extract, a fermented food product, cheese, garlic or extracts thereof, a gamma-glutamyl-containing polypeptide, a gamma-glutamyl-containing oligopeptide (such as gamma-glutamyl-containing tripeptides); an amide compound (such as a cinnamic acid amide or a derivative thereof), a nucleotide, an oligonucleotide, a plant extract, a food extract, or any combination thereof. In some embodiments, the kokumi tastant is a gamma-glutamyl-containing tripeptide. In some embodiments, the ingestible composition comprises the kokumi tastant at a lower concentration than an equally kokumi-tasting composition not comprising the amide compound (according to any of the embodiments set forth above). In some such embodiments, the concentration of the kokumi tastants is more than 10% less, more than 20% less, more than 30% less, more than 40% less, more than 50% less, more than 60% less, or more than 70% less, or more than 80% less, or more than 90% less than the concentration of kokumi tastants in an equally kokumi-tasting composition not comprising the amide compound (according to any of the embodiments set forth above). In some embodiments, the kokumi tastant is present in the ingestible composition at a concentration ranging from 1 ppm to 1000 ppm, or from 1 ppm to 900 ppm, or from 1 ppm to 800 ppm, or from 1 ppm to 700 ppm, or from 1 ppm to 600 ppm, or from 1 ppm to 500 ppm, or from 1 ppm to 400 ppm, or from 1 ppm to 300 ppm, or from 1 ppm to 200 ppm, or from 1 ppm to 100 ppm, or from 1 ppm to 75 ppm, or from 1 ppm to 50 ppm, or from 1 ppm to 25 ppm, or from 1 ppm to 10 ppm, based on the total weight of the ingestible composition.

In certain particular embodiments, the ingestible composition comprises alcohol, and the amide compound (according to any of the embodiments set forth above). In some such embodiments, the introduction of the amide compound permits one to use less alcohol (such as more than 10% less, more than 20% less, more than 30% less, more than 40% less, more than 50% less, more than 60% less, or more than 70% less, or more than 80% less, or more than 90% less) and still achieve a level of alcoholic characteristic of a comparable product that employs a higher concentration of alcohol but not the amide compound. In some related embodiments, the use of the amide compound permits the elimination of alcohol from the composition. The alcohol can have any suitable concentration in the ingestible compositions. In some embodiments, the alcohol concentration ranges from 1 percent by volume to 50 percent by volume, or from 1 percent by volume to 45 percent by volume, or from 1 percent by volume to 40 percent by volume, or from 1 percent by volume to 35 percent by volume, or from 1 percent by volume to 30 percent by volume, or from 1 percent by volume to 25 percent by volume, or from 1 percent by volume to 20 percent by volume, or from 1 percent by volume to 15 percent by volume, or from 1 percent by volume to 10 percent by volume, or from 1 percent by volume to 5 percent by volume, based on the total volume of the ingestible composition. In some embodiments, the ingestible composition comprises no more than 1 percent by volume alcohol, based on the total volume of the ingestible composition. Such ingestible compositions can be in any suitable form. In some embodiments, the ingestible composition is a food product, such as any of those specifically listed below. In other embodiments, the ingestible composition is a beverage product, such as a soda (such as a hard soda), and the like. The alcohol can present in any suitable form, such as alcohol formed from grains, cane sugar, fruits, and the like.

In some instances, one may be able to reduce the amount of sweetener in a product by enhancing the umami or kokumi taste. Thus, in some embodiments, the ingestible composition comprises one or more sweeteners according to any of the embodiments set forth below.

Such sweeteners can be present in any suitable amount. For example, in some embodiments, the sweetener is present in a concentration ranging from 0.1% to 12% by weight. In some embodiments, the sweetener is present in an amount from 0.2% to 10% by weight. In some embodiments, the sweetener is present in an amount from 0.3% to 8% by weight. In some embodiments, the sweetener is present in an amount from 0.4% to 6% by weight. In some embodiments, the sweetener is present in an amount from 0.5% to 5% by weight. In some embodiments, the sweetener is present in an amount from 10% to 2% by weight. In some embodiments, the sweetener is present in an amount from 0.1% to 5% by weight. In some embodiments, the sweetener is present in an amount from 0.10% to 4% by weight. In some embodiments, the sweetener is present in an amount from 0.1% to 3% by weight. In some embodiments, the sweetener is present in an amount from 0.10% to 2% by weight. In some embodiments, the sweetener is present in an amount from 0.10% to 1% by weight. In some embodiments, the sweetener is present in an amount from 0.1% to 0.5% by weight. In some embodiments, the sweetener is present in an amount from 0.5% to 10% by weight. In some embodiments, the sweetener is present in an amount from 2% to 8% by weight. In some further embodiments of the embodiments set forth in this paragraph, the sweetener is sucrose, fructose, glucose, xylitol, erythritol, or combinations thereof. The percentages set forth above are weight percent, based on the total weight of the ingestible composition.

In some other embodiments, the sweetener is present in an amount from 10 ppm to 1000 ppm. In some embodiments, the sweetener is present in an amount from 20 ppm to 800 ppm. In some embodiments, the sweetener is present in an amount from 30 ppm to 600 ppm. In some embodiments, the sweetener is present in an amount from 40 ppm to 500 ppm. In some embodiments, the sweetener is present in an amount from 50 ppm to 400 ppm. In some embodiments, the sweetener is present in an amount from 50 ppm to 300 ppm. In some embodiments, the sweetener is present in an amount from 50 ppm to 200 ppm. In some embodiments, the sweetener is present in an amount from 50 ppm to 150 ppm. In some further embodiments of the embodiments set forth in this paragraph, the sweetener is a steviol glycoside, a mogroside, a derivative of either of the foregoing, such as glycoside derivatives (e.g., glucosylates), or any combination thereof.

The compositions can include any suitable sweeteners or combination of sweeteners. In some embodiments, the sweetener is a common saccharide sweeteners, such as sucrose, fructose, glucose, and sweetener compositions comprising natural sugars, such as corn syrup (including high fructose corn syrup) or other syrups or sweetener concentrates derived from natural fruit and vegetable sources. In some embodiments, the sweetener is sucrose, fructose, or a combination thereof. In some embodiments, the sweetener is sucrose. In some other embodiments, the sweetener is selected from rare natural sugars including D-allose, D-psicose, L-ribose, D-tagatose, L-glucose, L-fucose, L-arbinose, D-turanose, and D-leucrose. In some embodiments, the sweetener is selected from semi-synthetic "sugar alcohol" sweeteners such as erythritol, isomalt, lactitol, mannitol, sorbitol, xylitol, maltodextrin, and the like. In some embodiments, the sweetener is selected from artificial sweeteners such as aspartame, saccharin, acesulfame-K, cyclamate, sucralose, and alitame. In some embodiments, the sweetener is selected from the group consisting of cyclamic acid, mogroside, tagatose, maltose, galactose, mannose, sucrose, fructose, lactose, allulose, neotame and other aspartame derivatives, glucose, D-tryptophan, glycine, maltitol, lactitol, isomalt, hydrogenated glucose syrup (HGS), hydrogenated starch hydrolyzate (HSH), stevioside, rebaudioside A, other sweet *Stevia*-based glycosides, chemically modified steviol glycosides (such as glucosylated steviol glycosides), mogrosides, chemically modified mogrosides (such as glucosylated mogrosides), carrelame and other guanidine-based sweeteners. In some embodiments, the sweetener is a combination of two or more of the sweeteners set forth in this paragraph. In some embodiments, the sweetener may combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a sugar. In some embodiments, the sugar is cane sugar. In some embodiments, the sugar is beet sugar. In some embodiments, the sugar may be sucrose, fructose, glucose or combinations thereof. In some embodiments, the sugar may be sucrose. In some embodiments, the sugar may be a combination of fructose and glucose.

The sweetener can also include, for example, sweetener compositions comprising one or more natural or synthetic carbohydrate, such as corn syrup, high fructose corn syrup, high maltose corn syrup, glucose syrup, sucralose syrup, hydrogenated glucose syrup (HGS), hydrogenated starch hydrolyzate (HSH), or other syrups or sweetener concentrates derived from natural fruit and vegetable sources, or semi-synthetic "sugar alcohol" sweeteners such as polyols. Non-limiting examples of polyols in some embodiments include erythritol, maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, isomaltulose, maltodextrin, and the like, and sugar alcohols or any other carbohydrates or combinations thereof capable of being reduced which do not adversely affect taste.

The sweetener may be a natural or synthetic sweetener that includes, but is not limited to, agave inulin, agave nectar, agave syrup, amazake, brazzein, brown rice syrup, coconut crystals, coconut sugars, coconut syrup, date sugar, fructans (also referred to as inulin fiber, fructo-oligosaccharides, or oligo-fructose), green *stevia* powder, *Stevia rebaudiana*, rebaudioside A, rebaudioside B, rebaudioside C, rebaudioside D, rebaudioside E, rebaudioside F, rebaudioside I, rebaudioside H, rebaudioside L, rebaudioside K, rebaudioside J, rebaudioside N, rebaudioside O, rebaudioside M and other sweet *stevia*-based glycosides, stevioside, stevioside extracts, honey, Jerusalem artichoke syrup, licorice root, luo han guo (fruit, powder, or extracts), lucuma (fruit, powder, or extracts), maple sap (including, for example, sap extracted from *Acer saccharum, Acer nigrum, Acer rubrum, Acer saccharinum, Acer platanoides, Acer negundo, Acer macrophyllum, Acer grandidentatum, Acer glabrum, Acer mono*), maple syrup, maple sugar, walnut sap (including, for example, sap extracted from *Juglans cinerea, Juglans nigra, Juglans ailatifolia, Juglans regia*), birch sap (including, for example, sap extracted from *Betula papyrif-*

*era, Betula alleghaniensis, Betula lenta, Betula nigra, Betula populifolia, Betula pendula*), sycamore sap (such as, for example, sap extracted from *Platanus* occidenta/is), ironwood sap (such as, for example, sap extracted from *Ostrya virginiana*), mascobado, molasses (such as, for example, blackstrap molasses), molasses sugar, monatin, monellin, cane sugar (also referred to as natural sugar, unrefined cane sugar, or sucrose), palm sugar, panocha, piloncillo, rapadura, raw sugar, rice syrup, sorghum, sorghum syrup, cassava syrup (also referred to as tapioca syrup), thaumatin, yacon root, malt syrup, barley malt syrup, barley malt powder, beet sugar, cane sugar, crystalline juice crystals, caramel, carbitol, carob syrup, castor sugar, hydrogenated starch hydrolates, hydrolyzed can juice, hydrolyzed starch, invert sugar, anethole, arabinogalactan, arrope, syrup, P-4000, acesulfame potassium (also referred to as acesulfame K or ace-K), alitame (also referred to as aclame), advantame, aspartame, baiyunoside, neotame, benzamide derivatives, bemadame, canderel, carrelame and other guanidine-based sweeteners, vegetable fiber, corn sugar, coupling sugars, curculin, cyclamates, cyclocarioside I, demerara, dextran, dextrin, diastatic malt, dulcin, sucrol, valzin, dulcoside A, dulcoside B, emulin, enoxolone, maltodextrin, saccharin, estragole, ethyl maltol, glucin, gluconic acid, glucono-lactone, glucosamine, glucoronic acid, glycerol, glycine, glycyphillin, glycyrrhizin, glycyrrhetic acid monoglucuronide, golden sugar, yellow sugar, golden syrup, granulated sugar, gynostemma, hernandulcin, isomerized liquid sugars, jallab, chicory root dietary fiber, kynurenine derivatives (including N'-formyl-kynurenine, N'-acetyl-kynurenine, 6-chloro-kynurenine), galactitol, litesse, ligicane, lycasin, lugduname, guanidine, falemum, mabinlin I, mabinlin II, maltol, maltisorb, maltodextrin, maltotriol, mannosamine, miraculin, mizuame, mogrosides (including, for example, mogroside IV, mogroside V, and neomogroside), mukurozioside, nano sugar, naringin dihydrochalcone, neohesperidine dihydrochalcone, nib sugar, nigero-oligosaccharide, norbu, orgeat syrup, osladin, pekmez, pentadin, periandrin I, perillaldehyde, perillartine, petphyllum, phenylalanine, phlomisoside I, phlorodizin, phyllodulcin, polyglycitol syrups, polypodoside A, pterocaryoside A, pterocaryoside B, rebiana, refiners syrup, rub syrup, rubusoside, selligueain A, shugr, siamenoside I, siraitia grosvenorii, soybean oligosaccharide, Splenda, SRI oxime V, steviol glycoside, steviolbioside, stevioside, strogins 1, 2, and 4, sucronic acid, sucrononate, sugar, suosan, phloridzin, superaspartame, tetrasaccharide, threitol, treacle, trilobtain, tryptophan and derivatives (6-trifluoromethyl-tryptophan, 6-chloro-D-tryptophan), vanilla sugar, volemitol, birch syrup, aspartame-acesulfame, assugrin, and combinations or blends of any two or more thereof.

In still other embodiments, the sweetener can be a chemically or enzymatically modified natural high potency sweetener. Modified natural high potency sweeteners include glycosylated natural high potency sweetener such as glucosyl-, galactosyl-, or fructosyl-derivatives containing 1-50 glycosidic residues. Glycosylated natural high potency sweeteners may be prepared by enzymatic transglycosylation reaction catalyzed by various enzymes possessing transglycosylating activity. In some embodiments, the modified sweetener can be substituted or unsubstituted.

Additional sweeteners also include combinations of any two or more of any of the aforementioned sweeteners. In some embodiments, the sweetener may comprise combinations of two, three, four or five sweeteners as disclosed herein. In some embodiments, the sweetener may be a sugar. In some embodiments, the sweetener may be a combination of one or more sugars and other natural and artificial sweeteners. In some embodiments, the sweetener is a caloric sweetener, such as sucrose, fructose, xylitol, erythritol, or combinations thereof. In some embodiments, the ingestible compositions are free (or, in some embodiments) substantially free of *stevia*-derived sweeteners, such as steviol glycosides, glucosylated steviol glycosides, or rebaudiosides. For example, in some embodiments, the ingestible compositions are either free of *stevia*-derived sweeteners or comprise *stevia*-derived sweeteners in a concentration of no more than 1000 ppm, or no more than 500 ppm, or no more than 200 ppm, or no more than 100 ppm, or no more than 50 ppm, or no more than 20 ppm, or no more than 10 ppm, or no more than 5 ppm, or no more than 3 ppm, or no more than 1 ppm.

The ingestible compositions can, in certain embodiments, comprise any additional ingredients or combination of ingredients as are commonly used in food and beverage products, including, but not limited to:

- acids, including, for example citric acid, phosphoric acid, ascorbic acid, sodium acid sulfate, lactic acid, or tartaric acid;
- bitter ingredients, including, for example caffeine, quinine, green tea, catechins, polyphenols, green *robusta* coffee extract, green coffee extract, potassium chloride, menthol, or proteins (such as proteins and protein isolates derived from plants, algae, or fungi);
- coloring agents, including, for example caramel color, Red #40, Yellow #5, Yellow #6, Blue #1, Red #3, purple carrot, black carrot juice, purple sweet potato, vegetable juice, fruit juice, beta carotene, turmeric curcumin, or titanium dioxide;
- preservatives, including, for example sodium benzoate, potassium benzoate, potassium sorbate, sodium metabisulfate, sorbic acid, or benzoic acid;
- antioxidants including, for example ascorbic acid, calcium disodium EDTA, alpha tocopherols, mixed tocopherols, rosemary extract, grape seed extract, resveratrol, or sodium hexametaphosphate;
- vitamins or functional ingredients including, for example resveratrol, Co-Q10, omega 3 fatty acids, theanine, choline chloride (citocoline), fibersol, inulin (chicory root), taurine, *panax ginseng* extract, guanana extract, ginger extract, L-phenylalanine, L-camitine, L-tartrate, D-glucoronolactone, inositol, bioflavonoids, *Echinacea*, ginko *biloba*, yerba mate, flax seed oil, garcinia cambogia rind extract, white tea extract, ribose, milk thistle extract, grape seed extract, pyrodixine HCl (vitamin B6), cyanoobalamin (vitamin B12), niacinamide (vitamin B3), biotin, calcium lactate, calcium pantothenate (pantothenic acid), calcium phosphate, calcium carbonate, chromium chloride, chromium polynicotinate, cupric sulfate, folic acid, ferric pyrophosphate, iron, magnesium lactate, magnesium carbonate, magnesium sulfate, monopotassium phosphate, monosodium phosphate, phosphorus, potassium iodide, potassium phosphate, riboflavin, sodium sulfate, sodium gluconate, sodium polyphosphate, sodium bicarbonate, thiamine mononitrate, vitamin D3, vitamin A palmitate, zinc gluconate, zinc lactate, or zinc sulphate;
- clouding agents, including, for example ester gun, brominated vegetable oil (BVO), or sucrose acetate isobutyrate (SAIB);
- buffers, including, for example sodium citrate, potassium citrate, or salt;
- flavors, including, for example propylene glycol, ethyl alcohol, glycerine, gum Arabic (gum acacia), maltodextrin, modified corn starch, dextrose, natural flavor, natural flavor with other natural flavors (natural flavor WONF), natural and artificial flavors, artificial flavor, silicon dioxide, magnesium carbonate, or tricalcium phosphate; or starches and stabilizers, including, for example pectin, xanthan gum, carboxylmethylcellulose (CMC), polysorbate 60, polysorbate 80, medium chain triglycerides, cellulose gel, cellulose gum, sodium caseinate, modified food starch, gum Arabic (gum acacia), inulin, or carrageenan.

The ingestible compositions can have any suitable pH. In some embodiments, the amide compounds enhance the sweetness of a sweetener under a broad range of pH, e.g., from lower pH to neutral pH. The lower and neutral pH includes, but is not limited to, a pH from 1.5 to 9.0, or from 2.5 to 8.5; from 3.0 to 8.0; from 3.5 to 7.5; and from 4.0 to 7. In certain embodiments, compounds as disclosed and described herein, individually or in combination, can enhance the perceived sweetness of a fixed concentration of a sweetener in taste tests at a compound concentration of 50 μM, 40 μM, 30 μM, 20 μM, or 10 μM at both low to neutral pH value. In certain embodiments, the enhancement factor of the compounds as disclosed and described herein, individually or in combination, at the lower pH is substantially similar to the enhancement factor of the compounds at neutral pH. Such consistent sweet enhancing property under a broad range of pH allow a broad use in a wide variety of foods and beverages of the compounds as disclosed and described herein, individually or in combination.

The ingestible compositions set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness or licorice taste, compounds that enhance saltiness, compounds that enhance a cooling effect, or any combinations of the foregoing.

Thus, in some embodiments, ingestible compositions disclosed herein the amide compound is combined with one or more sweetness enhancing compounds. Such sweetness enhancing compounds include, but are not limited to, naturally derived compounds, such as hesperitin, naringenin, rhoifolin, glucosylated steviol glycosides, licorice-derived glucuronates, aromadendrin-3-O-acetate, or other like flavonols, or flavonoids, or synthetic compounds, such as any compounds set forth in U.S. Pat. Nos. 8,541,421; 8,815,956; 9,834,544; 8,592,592; 8,877,922; 9,000,054; and 9,000,051, as well as U.S. Patent Application Publication No. 2017/0119032. The amide compound may be used in combination with such other sweetness enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1. In some embodiments of any of the preceding embodiments, the amide compound is combined with glucosylated steviol glycosides in any of the above ratios. As used herein, the term "glucosylated steviol glycoside" refers to the product of enzymatically glucosylating natural steviol glycoside compounds. The glucosylation generally occurs through a glycosidic bond, such as an α-1,2 bond, an α-1,4 bond, an α-1.6 bond, a β-1,2 bond, a β-1,4 bond, a β-1,6 bond, and so forth. In some embodiments of any of the preceding embodiments, the amide compound is combined with 3-((4-amino-2,2-dioxo-1H-benzo[c][1,2,6]thiadiazin-5-yl)oxy)-2,2-dimethyl-N-propyl-propanamide, N-(1-((4-amino-2,2-dioxo-1H-benzo[c][1,2,6]thiadiazin-5-yl)oxy)-2-methyl-propan-2-yl) isonicotinamide, or any combination thereof, in any of the above ratios.

In some further embodiments, ingestible compositions disclosed herein the amide compound is combined with one or more other umami or kokumi enhancing compounds. Such umami enhancing compounds include, but are not limited to, naturally derived compounds, such as ericamide, or synthetic compounds, such as any compounds set forth in U.S. Pat. Nos. 8,735,081; 8,124,121; and 8,968,708. The amide compound may be used in combination with such umami enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1,20:1,21:1,22:1,23:1,24:1, or 25:1.

In some further embodiments, ingestible compositions disclosed herein the amide compound is combined with one or more cooling enhancing compounds. Such cooling enhancing compounds include, but are not limited to, naturally derived compounds, such as menthol or analogs thereof, or synthetic compounds, such as any compounds set forth in U.S. Pat. Nos. 9,394,287 and 10,421,727. The amide compound may be used in combination with such cooling enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein the amide compound is combined with one or more bitterness blocking compounds. Such bitterness blocking compounds include, but are not limited to, naturally derived compounds, such as menthol or analogs thereof, or synthetic compounds, such as any compounds set forth in U.S. Pat. Nos. 8,076,491; 8,445,692; and 9,247,759. The amide compound may be used in combination with such bitterness blockers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1,20:1,21:1,22:1,23:1,24:1, or 25:1.

In some further embodiments, ingestible compositions disclosed herein the amide compound is combined with one or more sour taste modulating compounds. The amide compound may be used in combination with such sour taste modulating compounds in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein the amide compound is combined with one or more mouthfeel modifying compounds. Such mouthfeel modifying compounds include, but are not limited to, tannins, cellulosic materials, bamboo powder, and the like. The amide compound may be used in combination with such mouthfeel enhancers in any suitable ratio (w/w) ranging from 1:1000 to 1000:1, or from 1:100 to 100:1, or fro, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some further embodiments, ingestible compositions disclosed herein the amide compound is combined with one or more flavor masking compounds. Such flavor masking compounds include, but are not limited to, cellulosic materials, materials extracted from fungus, materials extracted from plants, citric acid, carbonic acid (or carbonates), and the like. The amide compound may be used in combination with such mouthfeel enhancers in any suitable ratio (w/w) ranging from 1:1000 to 1000:1, or from 1:100 to 100:1, or from, 1:50 to 50:1, or from 1:25 to 25:1, or from 1:10 to 10:1, such as 1:25, 1:24, 1:23, 1:22, 1:21, 1:20, 1:19, 1:18, 1:17, 1:16, 1:15, 1:14, 1:13, 1:12, 1:11, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, or 25:1.

In some aspects related to the preceding aspects and embodiments, the disclosure provides uses of the amide compound to enhance the flavor of a flavored composition, such as a flavored article. Such flavored compositions can use any suitable flavors, such as fruit flavors, meat flavors, vegetable flavors, and the like. In some embodiments, the flavored composition is a soup or broth, or a chip, or a beverage.

Flavored Products

In certain aspects, the disclosure provides flavored products comprising any compositions of the preceding aspects or embodiments thereof. In some embodiments, the flavored products are beverage products, such as soda, flavored water, tea, and the like. In some other embodiments, the flavored products are food products, such as yogurt, soup, meat analogues, dairy analogues, or the like.

In embodiments where the flavored product is a beverage, the beverage may be selected from the group consisting of enhanced sparkling beverages, colas, lemon-lime flavored sparkling beverages, orange flavored sparkling beverages, grape flavored sparkling beverages, strawberry flavored sparkling beverages, pineapple flavored sparkling beverages, ginger-ales, root beers, fruit juices, fruit-flavored juices, juice drinks, nectars, vegetable juices, vegetable-flavored juices, sports drinks, energy drinks, enhanced water drinks, enhanced water with vitamins, near water drinks, coconut waters, tea type drinks, coffees, cocoa drinks, beverages containing milk components, beverages containing cereal extracts and smoothies. In some embodiments, the beverage may be a soft drink.

In certain embodiments of any aspects and embodiments set forth herein that refer to a flavored product, the flavored product is a non-naturally-occurring product, such as a packaged food or beverage product.

Further non-limiting examples of food and beverage products or formulations include sweet coatings, frostings, or glazes for such products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionery category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups).

The Dehydrated and Culinary Food Category usually means: (i) Cooking aid products such as: powders, granules, pastes, concentrated liquid products, including concentrated bouillon, bouillon and bouillon like products in pressed cubes, tablets or powder or granulated form, which are sold separately as a finished product or as an ingredient within a product, sauces and recipe mixes (regardless of technology); (ii) Meal solutions products such as: dehydrated and freeze dried soups, including dehydrated soup mixes, dehydrated instant soups, dehydrated ready-to-cook soups, dehydrated or ambient preparations of ready-made dishes, meals and single serve entrees including pasta, potato and rice dishes; and (iii) Meal embellishment products such as: condiments, marinades, salad dressings, salad toppings, dips, breading, batter mixes, shelf stable spreads, barbecue sauces, liquid recipe mixes, concentrates, sauces or sauce mixes, including recipe mixes for salad, sold as a finished product or as an ingredient within a product, whether dehydrated, liquid or frozen.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes the alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionery category generally refers to edible product that is sweet to the taste. Examples of confectionery include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, dessert mixes, dried ready meals, dehydrated soup, instant soup, dried pasta, plain noodles, and instant noodles. The Chill Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, bouillon/stock cubes, herbs and spices, monosodium glutamate (MSG), table sauces, soy based sauces, pasta sauces, wet/cooking sauces, dry sauces/powder mixes, ketchup, mayonnaise, mustard, salad dressings, vinaigrettes, dips, pickled products, and other sauces, dressings and condiments.

The Baby Food category includes, but is not limited to milk- or soybean-based formula; and prepared, dried and other baby food.

The Spreads category includes, but is not limited to jams and preserves, honey, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for flavored products, particularly food and beverage products or formulations, are provided as follows. Exemplary ingestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorice, other sugar confectionery, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary ingestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof. Exemplary ingestible compositions also include breakfast cereals, sweet beverages or solid or liquid concentrate compositions for preparing beverages, ideally so as to enable the reduction in concentration of previously known saccharide sweeteners, or artificial sweeteners.

Some embodiments provide a chewable composition that may or may not be intended to be swallowed. In some embodiments, the chewable composition may be gum, chewing gum, sugarized gum, sugar-free gum, functional gum, bubble gum including compounds as disclosed and described herein, individually or in combination.

In some embodiments, the amide compound as disclosed and described herein, individually or in combination, may be provided in a flavoring concentrate formulation, e.g., suitable for subsequent processing to produce a ready-to-use (i.e., ready-to-serve) product. By "a flavoring concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The flavoring concentrate formulation is typically used by mixing with or diluted by one or more diluting medium, e.g., any consumable or ingestible ingredient or product, to impart or modify one or more flavors to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a soft drink syrup concentrate can be reconstituted with water or other aqueous medium by a manufacturer in large industrial scales to produce the ready-to-use soft drinks. Since the flavoring concentrate formulation has the flavoring agent or flavor modifying agent in a concentration higher than the ready-to-use composition, the flavoring concentrate formulation is typically not suitable for being consumed directly without reconstitution. There are many benefits of using and producing a flavoring concentrate formulation. For example, one benefit is the reduction in weight and volume for transportation as the flavoring concentrate formulation can be reconstituted at the time of usage by the addition of suitable solvent, solid or liquid.

The flavored products set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness, compounds that enhance umami, compounds that reduce sourness, compounds that enhance saltiness, compounds that enhance a cooling effect, or any combinations of the foregoing.

In certain embodiments of any aspects and embodiments set forth herein that refer to a sweetening or flavoring concentrate, the sweetening or flavoring concentrate is a non-naturally-occurring product, such as a composition specifically manufactured for the production of a flavored product, such as food or beverage product.

In one embodiment, the flavoring concentrate formulation comprises i) compounds as disclosed and described herein, individually or in combination; ii) a carrier; and iii) optionally at least one adjuvant. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the flavoring concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. The one or more sweeteners can be any of the sweeteners described in this application. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the content of which is hereby incorporated by reference in its entirety for all purposes.

In one embodiment, the present flavoring concentrate formulation can be in a form selected from the group consisting of liquid including solution and suspension, solid, foamy material, paste, gel, cream, and a combination thereof, such as a liquid containing certain amount of solid contents. In one embodiment, the flavoring concentrate formulation is in form of a liquid including aqueous-based and nonaqueous-based. In some embodiments, the present flavoring concentrate formulation can be carbonated or non-carbonated.

The flavoring concentrate formulation may further comprise a freezing point depressant, nucleating agent, or both as the at least one adjuvant. The freezing point depressant is an ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes an ingestibly acceptable compound or agent which is able to facilitate nucleation. The presence of nucleating agent in the flavoring concentrate formulation can improve the mouthfeel of the frozen Blushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the flavoring concentrate formulation is formulated to have a low water activity for extended shelf life. Water activity is the ratio of the vapor pressure of water in a formulation to the vapor pressure of pure water at the same temperature. In one embodiment, the flavoring concentrate formulation has a water activity of less than about 0.85. In another embodiment, the flavoring concentrate formulation has a water activity of less than about 0.80. In another embodiment, the flavoring concentrate formulation has a water activity of less than about 0.75.

In one embodiment, the flavoring concentrate formulation has the present compound in a concentration that is at least 2 times of the concentration of the compound in a ready-to-use composition. In one embodiment, the flavoring concentrate formulation has the present compound in a concentration that is at least 5 times of the concentration of the compound in a ready-to-use composition. In one embodiment, the flavoring concentrate formulation has the present compound in a concentration that is at least 10 times of the concentration of the compound in a ready-to-use composition. In one embodiment, the flavoring concentrate formulation has the present compound in a concentration that is at least 15 times of the concentration of the compound in a ready-to-use composition. In one embodiment, the flavoring concentrate formulation has the present compound in a concentration that is at least 20 times of the concentration of the compound in a ready-to-use composition. In one embodiment, the flavoring concentrate formulation has the present compound in a concentration that is at least 30 times of the concentration of the compound in a ready-to-use composition. In one embodiment, the flavoring concentrate formulation has the present compound in a concentration that is at least 40 times of the concentration of the compound in a ready-to-use composition. In one embodiment, the flavoring concentrate formulation has the present compound in a concentration that is at least 50 times of the concentration of the compound in a ready-to-use composition. In one embodiment, the flavoring concentrate formulation has the present compound in a concentration that is at least 60 times of the concentration of the compound in a ready-to-use composition. In one embodiment, the flavoring concentrate formulation has the present compound in a concentration that is up to 100 times of the concentration of the compound in a ready-to-use composition.

The sweetening or flavoring concentrates set forth according to any of the foregoing embodiments, also include, in certain embodiments, one or more additional flavor-modifying compounds, such as compounds that enhance sweetness (e.g., hesperetin, naringenin, glucosylated steviol glycosides, etc.), compounds that block bitterness (e.g., eriodictyol, homoeriodictyol, sterubin, and salts or glycoside derivatives thereof, as well as vanillyl lignans, e.g., matairesinol and other compounds set forth in PCT Publication No. WO 2012/146584), compounds that enhance umami (e.g., rubemamine, rubescenamine, (E)-3-(3,4-dimethoxyphenyl)-N-(4-methoxyphenethyl)acrylamide, and the like), compounds that reduce sourness and/or licorice taste, compounds that enhance saltiness, compounds that enhance a cooling effect, or any combinations of the foregoing.

Packaged Flavoring Compositions

In some further aspects, the disclosure provides a packaged flavoring composition comprising: (a) an amide compound (according to any of the embodiments set forth above); and (b) at least one bulking agent.

The packaged flavoring composition may take any suitable form including, but not limited to, an amorphous solid, a crystal, a powder, a tablet, a liquid, a cube, a glace or coating, a granulated product, an encapsulated form abound to or coated on to carriers/particles, wet or dried, or combinations thereof.

The packaged flavoring composition may contain further additives known to those skilled in the art. These additives include but are not limited to bubble forming agents, bulking agents, carriers, fibers, sugar alcohols, oligosaccharides, sugars, high intensity sweeteners, nutritive sweeteners, flavorings, flavor enhancers, flavor stabilizers, acidulants, anti-caking and free-flow agents. Such additives are for example described by H. Mitchell (H. Mitchell, "Sweeteners and Sugar Alternatives in Food Technology", Blackwell Publishing Ltd, 2006, which is incorporated herein by reference in its entirety). As used herein, the term "flavorings" may include those flavors known to the skilled person, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, Japanese mint oil, clove oil, bay oil, anise oil, *eucalyptus* oil, thyme oil, cedar leaf oil, oil of nutmeg, allspice, oil of sage, mace, oil of bitter almonds, and *cassia* oil. Also useful flavorings are artificial, natural and synthetic fruit flavors such as vanilla, and citrus oils including lemon, orange, lime, grapefruit, yazu, sudachi, and fruit essences including apple, pear, peach, grape, blueberry, strawberry, raspberry, cherry, plum, pineapple, watermelon, apricot, banana, melon, apricot, ume, cherry, raspberry, blackberry, tropical fruit, mango, mangosteen, pomegranate, *papaya* and so forth. Other potential flavors include a milk flavor, a butter flavor, a cheese flavor, a cream flavor, and a yogurt flavor; a vanilla flavor; tea or coffee flavors, such as a green tea flavor, a oolong tea flavor, a tea flavor, a cocoa flavor, a chocolate flavor, and a coffee flavor; mint flavors, such as a peppermint flavor, a spearmint flavor, and a Japanese mint flavor; spicy flavors, such as an asafetida flavor, an ajowan flavor, an anise flavor, an *angelica* flavor, a fennel flavor, an allspice flavor, a cinnamon flavor, a camomile flavor, a mustard flavor, a cardamom flavor, a caraway flavor, a cumin flavor, a clove flavor, a pepper flavor, a coriander flavor, a *sassafras* flavor, a savory flavor, a Zanthoxyli Fructus flavor, a *perilla* flavor, a juniper berry flavor, a ginger flavor, a star anise flavor, a horseradish flavor, a thyme flavor, a tarragon flavor, a dill flavor, a *capsicum* flavor, a nutmeg flavor, a basil flavor, a marjoram flavor, a rosemary flavor, a bayleaf flavor, and a wasabi (Japanese horseradish) flavor; alcoholic flavors, such as a wine flavor, a whisky flavor, a brandy flavor, a rum flavor, a gin flavor, and a liqueur flavor; floral flavors; and vegetable flavors, such as an onion flavor, a garlic flavor, a cabbage flavor, a carrot flavor, a celery flavor, mushroom flavor, and a tomato flavor. These flavoring agents may be used in liquid or solid form and may be used individually or in admixture. Commonly used flavors include mints such as peppermint, menthol, spearmint, artificial vanilla, cinnamon derivatives, and various fruit flavors, whether employed individually or in admixture. Flavors may also provide breath freshening properties, particularly the mint flavors when used in combination with cooling agents.

Flavors may also provide breath freshening properties, particularly the mint flavors when used in combination with cooling agents. These flavorings may be used in liquid or solid form and may be used individually or in admixture. Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in Chemicals Used in Food Processing, publication 1274, pages 63-258, by the National Academy of Sciences, may be used. This publication is incorporated herein by reference.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, and mixtures thereof. These listings of flavorings are merely exemplary and are not meant to limit either the term "flavoring" or the scope of the disclosure generally.

In some embodiments, the flavoring may be employed in either liquid form and/or dried form. When employed in the latter form, suitable drying means such as spray drying the oil may be used. Alternatively, the flavoring may be absorbed onto water soluble materials, such as cellulose, starch, sugar, maltodextrin, gum arabic and so forth or may be encapsulated. The actual techniques for preparing such dried forms are well-known.

In some embodiments, the tabletop sweetener can be made to be similar to brown sugar. In such embodiments, compounds imparting brown notes can be added to the composition to make it taste more similar to brown sugar.

In some embodiments, the flavorings may be used in many distinct physical forms well-known in the art to provide an initial burst of flavor and/or a prolonged sensation of flavor. Without being limited thereto, such physical forms include free forms, such as spray dried, powdered, beaded forms, encapsulated forms, and mixtures thereof.

Suitable bulking agents include, but are not limited to maltodextrin (10 DE, 18 DE, or 5 DE), corn syrup solids (20 or 36 DE), sucrose, fructose, glucose, invert sugar, sorbitol, xylose, ribulose, mannose, xylitol, mannitol, galactitol, erythritol, maltitol, lactitol, isomalt, maltose, tagatose, lactose, inulin, glycerol, propylene glycol, polyols, polydextrose, fructooligosaccharides, cellulose and cellulose derivatives, and the like, and mixtures thereof. Additionally, granulated sugar (sucrose) or other caloric sweeteners such as crystalline fructose, other carbohydrates, or sugar alcohols can be used as a bulking agent due to their provision of good content uniformity without the addition of significant calories.

In one embodiment, the at least one bulking agent may be a bulking agent described in U.S. Pat. No. 8,993,027.

In one embodiment, the at least one bulking agent may be a bulking agent described in U.S. Pat. No. 6,607,771.

In one embodiment, the at least one bulking agent may be a bulking agent described in U.S. Pat. No. 6,932,982.

In some embodiments, the tabletop sweetener composition may further comprise at least one anti-caking agent. As used herein the phrase "anti-caking agent" and "flow agent" refer to any composition which prevents, reduces, inhibits, or suppresses the at least one sweetener from attaching, binding, or contacting to another sweetener molecule. Alternatively, anti-caking agent may refer to any composition which assists in content uniformity and uniform dissolution. Non-limiting examples of anti-caking agents include cream of tartar, calcium silicate, silicon dioxide, microcrystalline cellulose (Avicel, FMC BioPolymer, Philadelphia, Pa.), and tricalcium phosphate. In one embodiment, the anti-caking agents are present in the tabletop sweetener composition in an amount from about 0.001 to about 3% by weight of the tabletop sweetener composition.

In some embodiments, the sweetener compositions of any of the preceding aspects and embodiments thereof are encapsulated using typical means for encapsulating flavor or fragrance compounds. Non-limiting examples of such technology are set forth in U.S. Patent Application Publication Nos. 2016/0235102, 2019/0082727, 2018/0369777, 2018/0103667, 2016/0346752, 2015/0164117, 2014/0056836, 2012/0027866, 2010/0172945, and 2007/0128234, as well as U.S. Pat. Nos. 7,488,503, 6,416,799, 5,897,897, 5,786,017, 5,603,971, 4,689,235, 4,610,890, 3,704,137, 3,041,180, and 2,809,895. All of the preceding patent publications and patents are hereby incorporated by reference as though set forth herein in their entireties.

Non-Animal Protein Materials and Products Made Therefrom

Products intended to replace or substitute meat or dairy products often rely on various non-animal-based materials, such as fibers and proteins derived from plants, algae, or fungi, to simulate the texture and flavor of meat or dairy. Non-limiting examples of such plant proteins include soy proteins, pea proteins, bean proteins, grain proteins, and the like. Due to compositional differences between such plant-based materials and animal-derived materials, such as a lack of glutamate-containing proteins and glutathione, these products can lack the umami or kokumi taste that consumers traditionally associate with meat or dairy products.

Thus, in certain aspects, the disclosure provides a flavored product comprising a plant-based material (such as a plant-based starch, a plant-based protein, or a combination thereof) and an amide compound (according to any aspects and embodiments set forth above). In some further embodiments, the flavored product can include any features of combination of features set forth above for ingestible compositions that contain the amide compound. In some embodiments, the flavored product is a beverage, such as soy milk, almond milk, rice milk, oat milk, a protein drink, a meal-replacement drink, or other like product. In some other embodiments, the flavored product is a meat-replacement product, such as a plant-based chicken product (such as a plant-based chicken nugget), a plant-based beef product (such as a plant-based burger), and the like. In some other embodiments, the flavored product is a protein powder, a meal-replacement powder, a plant-based creamer for coffee or tea, and the like. In certain further embodiments, any such flavored products contain additional ingredients, and have additional features, as are typically used in the preparation and/or manufacture of such products. For example, such an amide compound (according to any of the embodiments set forth above) may be combined with other flavors and taste modifiers, and may even be encapsulated in certain materials, according to known technologies in the relevant art. Suitable concentrations of the amide compound are set forth above.

In some further embodiments analogous to the above embodiments, proteins or starches from algal or fungal sources can be used instead of or in combination with plant starches or proteins.

Non-Meat Protein Materials and Products Made Therefrom

Certain non-meat animal proteins, such as dairy proteins and proteins from bone broth, are commonly used in food products, and are also sold as the primary ingredient in certain protein powders. Such proteins can impart flavors that lack the full umami or kokumi taste that consumers may desire. This is especially true for protein isolates, such as protein isolates of whey protein, collagen protein, casein proteins, and the like. Thus, the present disclosure provides ingestible compositions that include non-meat animal proteins and the amide compound (according to any aspects and embodiments set forth above). The amide compound can be present in any suitable combination, according to the embodiments set forth in the preceding sections of the present disclosure. In some embodiments, the non-meat animal protein is a bone protein, such as a collagen protein derived from the bones of an animal, such as a cow, pig, donkey, horse, chicken, duck, goat, goose, rabbit, lamb, sheep, buffalo, ostrich, camel, and the like. In some embodiments, the non-meat animal protein is a milk protein, such as a whey protein, a casein protein, or any combination thereof. The milk can be the milk of any suitable animal, such as a cow, donkey, horse, sheep, buffalo, camel, and the like.

The amide compounds can also be included in certain food or beverage products that include animal milk or materials derived from animal milk. Such products include cheeses, cheese spreads, yogurt, kefir, milk, processed dairy products, cottage cheese, sour cream, butter, and the like.

Methods of Preparation

The compounds disclosed herein may be synthesized by methods described below, or by modification of these methods. Ways of modifying the methodology include, among others, temperature, solvent, reagents etc., known to those skilled in the art. In general, during any of the processes for preparation of the compounds disclosed herein, it may be necessary or desirable to protect sensitive or reactive groups on any of the molecules concerned.

EXAMPLES

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

Example 1: Synthesis of Ethyl (S)-2,5-Bis(Benzamido)Pentanoate

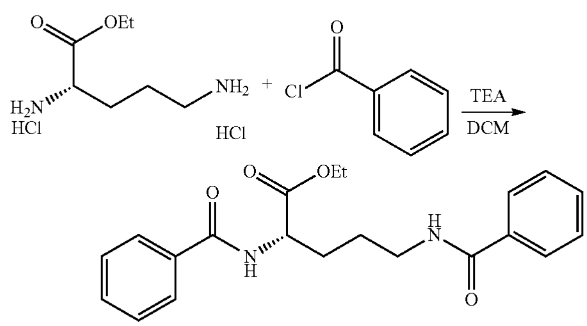

To a solution of L-ornithine ethyl ester dihydrochloride (164 mg, 0.703 mmol) and triethylamine (392 uL, 2.814 mmol) in dry DCM (5 mL) was added benzoyl chloride (164 uL, 1.406 mmol). The solution was stirred at room temperature overnight, diluted with DCM and washed successively with 1N HCl, saturated $NaHCO_3$, water, and brine. The organic layer was dried over Na2SO4 and concentrated. The crude residue was purified via silica gel chromatography in a 0-100% EtOAc/Hexanes gradient. The cleanest fractions were concentrated via rotary evaporation and repurified via preparatory HPLC (ACN/water as modifier). The clean fractions were concentrated down via rotary evaporation. The material was dissolved in EtOH and water and dried lyophilized overnight to afford ethyl (S)-2,5-bis(benzamido) pentanoate (SID 62763285) as a fluffy white powder (108 mg, 42% yield). 1H NMR (400 MHz, d6-DMSO) δ 1.18 (t, J=7.1 Hz, 3H), 1.64 (m, 2H), 1.84 (m, 2H), 3.25 (q, J=4.0 Hz, 2H), 4.10 (qd, J=7.1, 2.2 Hz, 2H), 4.43 (ddd, J=9.4, 7.4, 5.5 Hz, 1H), 7.40-7.60 (m, 6H), 7.80-7.85 (m, 2H), 7.85-7.92 (m, 2H), 8.48 (t, J=5.6 Hz, 1H), 8.75 (d, J=7.4 Hz, 1H). MS 369 (MH+).

Example 2: Synthesis of Methyl (S)-2-Cinnamamido-5-((E)-2-Methylbut-2-Enamido)-Pentanoate

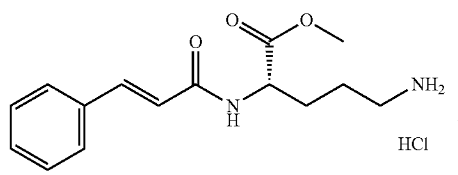

+

-continued

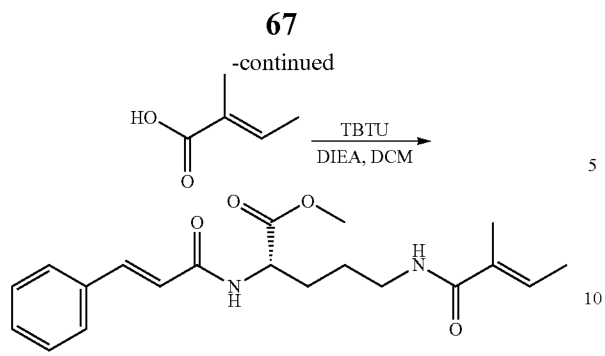

To a solution of tiglic acid (32 mg, 0.320 mmol) in anhydrous DCM 3 mL was added TBTU (134 mg, 0.416 mmol), methyl (S)-5-amino-2-cinnamamidopentanoate HCl salt (Example 2a, 100 mg, 0.320 mmol), and DIEA (111 uL, 0.640 mmol). The solution was stirred at room temperature for 16 hours and then purified via silica gel column chromatography in a 0-50% EtOAc/Hexanes gradient. The cleanest fractions were concentrated down via rotary evaporation to afford methyl (S)-2-cinnamamido-5-((E)-2-methylbut-2-enamido)pentanoate as a white solid (67 mg, 58% yield). MS 359 (MH+). $^1$H NMR (400 MHz, DMSO-d6) δ 1.48-1.62 (m, 4H), 1.69 (d, J=8.0 Hz, 3H), 1.72 (s, 3H), 3.10 (q, J=6.6 Hz, 2H), 3.64 (s, 3H), 4.35-4.40 (m, 1H), 6.20-6.34 (m, 1H), 6.72 (d, J=15.9 Hz, 1H), 7.34-7.50 (m, 4H), 7.54-7.61 (m, 2H), 7.77 (t, J=5.6 Hz, 1H), 8.52 (d, J=7.5 Hz, 1H). MS 359 (MH+).

Example 2a: Synthesis of Methyl (S)-5-Amino-2-Cinnamamidopentanoate HCl Salt

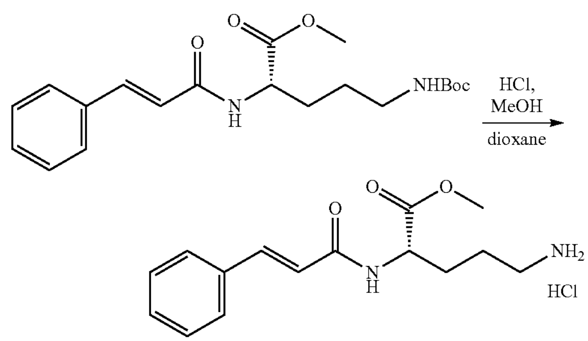

To a solution of methyl (S)-5-((tert-butoxycarbonyl)amino)-2-cinnamamidopentanoate (Example 2b, 365 mg, 0.970 mmol) in MeOH (3 mL) was added 4N HCl in dioxane (1 mL) and the solution was stirred at room temperature for 48 hours. The solution was concentrated via rotary evaporation to afford methyl (S)-5-amino-2-cinnamamidopentanoate HCl salt as an orange oil (372 mg, quantitative yield). MS 277 (MH+).

Example 2b: Synthesis of Methyl (S)-5-((Tert-Butoxycarbonyl)Amino)-2-Cinnamamido-Pentanoate

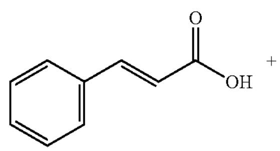

-continued

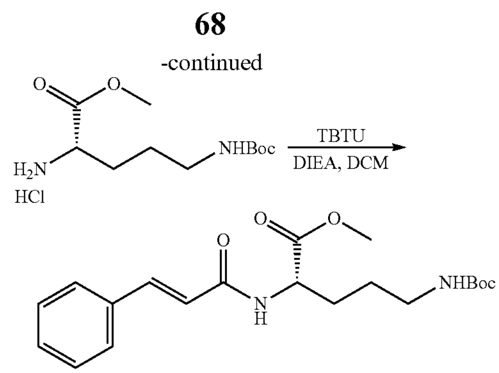

To a solution of trans-cinnamic acid (131 mg, 0.884 mmol) in dry DCM (5 mL) was added TBTU (369 mg, 1.149 mmol), methyl (S)-2-amino-5-((tert-butoxycarbonyl)amino) pentanoate HCl salt (250 mg, 0.884 mmol), and DIEA (308 uL, 1.768 mmol). The solution was stirred at room temperature for 16 hours and purified twice via silica gel column chromatography in a 0-30% EtOAc/Hexanes gradient. The clean fractions were concentrated via rotary evaporation to afford methyl (S)-5-((tert-butoxycarbonyl)amino)-2-cinnamamidopentanoate as a white solid (365 mg, quantitative yield). $^1$H NMR (400 MHz, DMSO-d6) δ 1.37 (s, 9H), 1.40-1.52 (m, 2H), 1.63-1.73 (m, 2H), 2.92 (q, J=4.0 Hz, 2H), 3.64 (s, 3H), 4.36 (m, 1H), 6.72 (d, J=15.9 Hz, 1H), 6.84 (t, J=8.0 Hz, 1H), 7.39-7.46 (m, 5H), 7.58 (m, 1H), 8.50 (d, J=7.5 Hz, 1H). MS 277 ($MH^+$–Boc).

Example 3—Compound Testing

Each of the compounds set forth in Table 2 were synthesized according to one of the general procedures set forth above in Example 1 or 2. Thereafter, the compounds were tested in an in vitro cell-based assay having cells that express the T1R umami taste receptor. Dose-binding curves were recorded and the EC50 was determined for enhancement of MSG binding. Table 2 sets forth the calculated EC50 values for certain tested compounds.

TABLE 2

| Compound | EC50 (μM) |
|---|---|
| 101 | >50 |
| 102 | 30 |
| 103 | 2.0 |
| 104 | 14 |
| 105 | 35 |
| 106 | 3.5 |
| 107 | 8.0 |
| 108 | 2.5 |
| 109 | 1.5 |
| 110 | 0.7 |
| 111 | 0.4 |
| 112 | <0.1 |
| 113 | 0.5 |
| 114 | 0.4 |
| 115 | 0.04 |
| 121 | 0.5 |
| 122 | 0.2 |
| 123 | 0.6 |
| 124 | 0.5 |
| 128 | 0.64 |
| 129 | 0.06 |
| 132 | 0.1 |
| 133 | 0.4 |

The invention claimed is:

1. A method of enhancing a salty, umami, or kokumi taste of an ingestible composition, the method comprising introducing to the ingestible composition a flavor-modifying compound, wherein the flavor-modifying compound is a compound of formula (I):

(I)

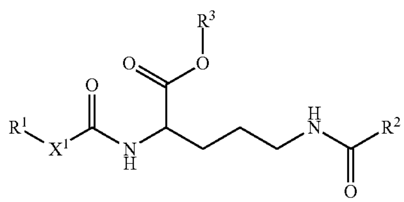

or a comestibly acceptable salt thereof;

wherein:

$R^1$ is $C_{6-14}$ aryl or $C_{4-12}$ heteroaryl, each of which is optionally substituted one or more times by substituents selected independently from the group consisting of $R^Y$;

$R^2$ is a $C_{1-10}$ alkyl, $C_{2-10}$ alkenyl, $C_{6-14}$ aryl, or $C_{1-12}$ heteroaryl, wherein the alkyl and alkenyl groups are each optionally substituted one or more times by substituents selected independently from the group consisting of $R^x$, and wherein the aryl and heteroaryl groups are each optionally substituted one or more times by substituents selected independently from the group consisting of $R^Y$;

$R^3$ is a hydrogen atom or is $C_{1-6}$ alkyl, which is optionally substituted one or more times by —OH, —O—($C_{1-6}$ alkyl), or any combination thereof;

$X^1$ is a direct bond, $C_{1-6}$ alkylene, or $C_{2-6}$ alkenylene, wherein the alkylene and alkenylene groups are each optionally substituted one or more times by substituents selected independently from the group consisting of $R^x$;

$R^x$ is a halogen atom, oxo, —CN, nitro, —OH, —$NH_2$, —C(O) H, —O—C(O) H, —C(O)—OH, —NH—C(O) H, —C(O)—$NH_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, and ($C_{1-6}$ alkoxy)-$C_{1-6}$ alkyl; and $R^Y$ is a halogen atom, oxo, —CN, nitro, —OH, —$NH_2$, —C(O) H, —O—C(O) H, —C(O)—OH, —NH—C(O) H, —C(O)—$NH_2$, —O—($C_{1-6}$ alkyl), —NH—($C_{1-6}$ alkyl), —N($C_{1-6}$ alkyl)$_2$, —C(O)—($C_{1-6}$ alkyl), —O—C(O)—($C_{1-6}$ alkyl), —NH—C(O)—($C_{1-6}$ alkyl), —C(O)—O—($C_{1-6}$ alkyl), —C(O)—NH—($C_{1-6}$ alkyl), —C(O)—N($C_{1-6}$ alkyl)$_2$, —S(O)$_2$—($C_{1-6}$ alkyl), —O—S(O)$_2$—($C_{1-6}$ alkyl), —NH—S(O)$_2$—($C_{1-6}$ alkyl), —S(O)$_2$—O—($C_{1-6}$ alkyl), —S(O)$_2$—NH—($C_{1-6}$ alkyl), —S(O)$_2$—N($C_{1-6}$ alkyl)$_2$, $C_{3-10}$ cycloalkyl, $C_{2-14}$ heterocyclyl, $C_{6-14}$ aryl, $C_{2-14}$ heteroaryl, $C_{1-6}$ alkyl, $C_{2-6}$ alkenyl, $C_{1-6}$ haloalkyl, $C_{2-6}$ haloalkenyl, $C_{1-6}$ haloalkoxy, $C_{2-6}$ haloalkenyloxy, ($C_{1-6}$ alkoxy)-$C_{1-6}$ alkyl, $C_{1-6}$ alkyl, and $C_{2-6}$ alkenyl, wherein any adjacent substituents on an aryl or heteroaryl ring can optionally combine to form a fused carbocyclic or heterocyclic ring having from 5 to 7 members.

2. The method of claim 1, wherein $X^1$ is a direct bond.

3. The method of claim 1, wherein $R^1$ is phenyl, which is substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring.

4. The method of claim 1, wherein $R^1$ is unsubstituted phenyl.

5. The method of claim 1, wherein $R^2$ is phenyl, which is substituted one or more times by substituents selected independently from the group consisting of —OH, —O—($C_{1-6}$ alkyl), and $C_{1-6}$ alkyl, wherein any two substituents on adjacent carbons of the phenyl ring can optionally combine to form a methylenedioxy fused ring.

6. The method of claim 1, wherein $R^2$ is unsubstituted phenyl.

7. The method of claim 1, wherein $R^3$ is a hydrogen atom or is an unsubstituted $C_{1-6}$ alkyl group.

8. The method of claim 1, wherein the flavor-modifying compound is a compound of formula (Ia)

(Ia)

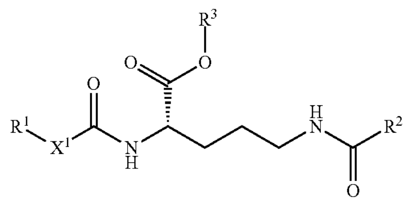

or a comestibly acceptable salt thereof.

9. The method of claim 8, wherein the flavor-modifying compound is (S)-2,5-bis(benzamido)pentanoic acidy, methyl (S)-2,5-bis(benzamido)pentanoate, methyl (S)-2,5-bis(benzamido)pentanoate, or a comestibly acceptable salt thereof.

10. The method of claim 1, wherein the method is a method of enhancing a salty taste of an ingestible composition.

11. The method of claim 1, wherein the method is a method of enhancing an umami taste of an ingestible composition.

12. The method of claim 1, wherein the method is a method of enhancing a kokumi taste of an ingestible composition.

13. The method of claim 1, wherein the ingestible composition comprises a salty tastant, an umami tastant, a kokumi tastant, or any combination thereof.

* * * * *